US011179136B2

(12) United States Patent
Kohli et al.

(10) Patent No.: US 11,179,136 B2
(45) Date of Patent: *Nov. 23, 2021

(54) LOUPE DISPLAY

(71) Applicant: InnerOptic Technology, Inc., Hillsborough, NC (US)

(72) Inventors: Luv Kohli, Durham, NC (US); Sharif Razzaque, Boulder, CO (US); Andrei State, Chapel Hill, NC (US); Brian Heaney, Durham, NC (US); Kurtis Keller, Hillsborough, NC (US); Caroline Green, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,628

(22) Filed: Oct. 7, 2019

(65) Prior Publication Data

US 2020/0138402 A1      May 7, 2020

Related U.S. Application Data

(63) Continuation of application No. 15/611,454, filed on Jun. 1, 2017, now Pat. No. 10,433,814, which is a (Continued)

(51) Int. Cl.
*A61B 8/00* (2006.01)
*A61B 8/08* (2006.01)
(Continued)

(52) U.S. Cl.
CPC .......... *A61B 8/0841* (2013.01); *A61B 5/0066* (2013.01); *A61B 5/055* (2013.01); (Continued)

(58) Field of Classification Search
CPC ....... A61B 5/0066; A61B 5/055; A61B 5/742; A61B 6/032; A61B 6/037; A61B 6/12; (Continued)

(56) References Cited

U.S. PATENT DOCUMENTS 3,556,079 A    1/1971 Omizo
4,058,114 A   11/1977 Soldner
(Continued)

FOREIGN PATENT DOCUMENTS

EP    0 427 358    5/1991
EP    1955284      8/2008
(Continued)

OTHER PUBLICATIONS

U.S. Appl. No. 11/828,826 including its ongoing prosecution history, including without limitation Office Actions, Amendments, Remarks, and any other potentially relevant document, dated Jul. 26, 2007, Keller et al.
(Continued)

*Primary Examiner* — Towfiq Elahi
(74) *Attorney, Agent, or Firm* — Knobbe, Martens, Olson & Bear, LLP

(57) ABSTRACT

A system and method for providing image guidance for placement of one or more medical devices at a target location. The system can determine one or more intersections between a medical device and an image region based at least in part on first emplacement data and second emplacement data. Using the determined intersections, the system can cause one or more displays to display perspective views of image guidance cues, including an intersection indicator in a virtual 3D space.

20 Claims, 11 Drawing Sheets

Related U.S. Application Data continuation of application No. 15/199,630, filed on Jun. 30, 2016, now Pat. No. 9,675,319.

(60) Provisional application No. 62/296,440, filed on Feb. 17, 2016.

(51) Int. Cl.
*A61B 6/03* (2006.01)
*A61B 5/055* (2006.01)
*A61B 5/00* (2006.01)
*A61B 6/00* (2006.01)
*A61B 5/06* (2006.01)

(52) U.S. Cl.
CPC .............. *A61B 6/032* (2013.01); *A61B 6/037* (2013.01); *A61B 6/466* (2013.01); *A61B 6/487* (2013.01); *A61B 8/4245* (2013.01); *A61B 8/466* (2013.01); *A61B 8/483* (2013.01); *A61B 5/066* (2013.01)

(58) Field of Classification Search
CPC ......... A61B 6/466; A61B 6/487; A61B 8/483; G06T 19/006
See application file for complete search history.

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldron |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,156,144 A | 10/1992 | Iwasaki et al. |
| 5,158,088 A | 10/1992 | Nelson et al. |
| 5,161,536 A | 11/1992 | Vilkomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,806,521 A | 9/1998 | Morimoto et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |

(56) References Cited

U.S. PATENT DOCUMENTS

| | | |
|---|---|---|
| 6,246,784 B1 | 6/2001 | Summers et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,547,777 B2 | 4/2003 | Resta et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,265,572 B2 | 2/2016 | Fuchs et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 10,026,191 B2 | 7/2018 | Accomando et al. |
| 10,127,629 B2 | 11/2018 | Razzaque et al. |
| 10,136,951 B2 | 11/2018 | Razzaque et al. |
| 10,188,467 B2 | 1/2019 | Razzaque et al. |
| 10,278,778 B2 | 5/2019 | State et al. |
| 10,314,559 B2 | 6/2019 | Razzaque et al. |
| 10,398,513 B2 | 9/2019 | Razzaque et al. |
| 10,433,814 B2 | 10/2019 | Razzaque et al. |
| 10,733,700 B2 | 8/2020 | Keller et al. |
| 10,772,686 B2 | 9/2020 | State et al. |
| 10,820,944 B2 | 11/2020 | State et al. |
| 10,820,946 B2 | 11/2020 | Heaney et al. |
| 11,103,200 B2 | 8/2021 | Kohli et al. |

(56) References Cited

U.S. PATENT DOCUMENTS

| | | |
|---|---|---|
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessman et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0033160 A1 | 2/2005 | Yamagata et al. |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0004275 A1 | 6/2006 | Vija et al. |
| 2006/0122495 A1 | 6/2006 | Kienzle |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1* | 2/2011 | Fuchs ............... A61B 8/4416 600/439 |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |

(56) References Cited

U.S. PATENT DOCUMENTS

| | | | |
|---|---|---|---|
| 2012/0035473 A1 | 2/2012 | Sanghvi et al. | |
| 2012/0059260 A1 | 3/2012 | Robinson | |
| 2012/0071759 A1 | 3/2012 | Hagy et al. | |
| 2012/0078094 A1 | 3/2012 | Nishina et al. | |
| 2012/0101370 A1* | 4/2012 | Razzaque | A61B 18/1477 |
| | | | 600/424 |
| 2012/0108955 A1 | 5/2012 | Razzaque et al. | |
| 2012/0138658 A1 | 6/2012 | Ullrich et al. | |
| 2012/0143029 A1 | 6/2012 | Silverstein et al. | |
| 2012/0143055 A1 | 6/2012 | Ng et al. | |
| 2012/0165679 A1 | 6/2012 | Orome et al. | |
| 2012/0215096 A1 | 8/2012 | Gilboa | |
| 2012/0230559 A1 | 9/2012 | Itai | |
| 2012/0237105 A1 | 9/2012 | Mielekamp | |
| 2012/0259210 A1 | 10/2012 | Harhen et al. | |
| 2013/0030286 A1 | 1/2013 | Alouani et al. | |
| 2013/0044930 A1 | 2/2013 | Li et al. | |
| 2013/0079770 A1 | 3/2013 | Kyle, Jr. et al. | |
| 2013/0090646 A1 | 4/2013 | Moss et al. | |
| 2013/0096497 A1 | 4/2013 | Duindam et al. | |
| 2013/0132374 A1 | 5/2013 | Olstad et al. | |
| 2013/0144165 A1 | 6/2013 | Ebbini et al. | |
| 2013/0151533 A1 | 6/2013 | Udupa et al. | |
| 2013/0178745 A1 | 7/2013 | Kyle et al. | |
| 2013/0218024 A1 | 8/2013 | Boctor et al. | |
| 2013/0249787 A1 | 9/2013 | Morimoto | |
| 2014/0051987 A1 | 2/2014 | Kowshik et al. | |
| 2014/0058387 A1 | 2/2014 | Kruecker et al. | |
| 2014/0078138 A1 | 3/2014 | Martin et al. | |
| 2014/0142426 A1* | 5/2014 | Razzaque | A61B 8/4245 |
| | | | 600/424 |
| 2014/0180074 A1 | 6/2014 | Green | |
| 2014/0201669 A1 | 7/2014 | Liu et al. | |
| 2014/0275760 A1 | 9/2014 | Lee et al. | |
| 2014/0275810 A1 | 9/2014 | Keller et al. | |
| 2014/0275997 A1 | 9/2014 | Chopra et al. | |
| 2014/0343404 A1 | 11/2014 | Razzaque et al. | |
| 2014/0350390 A1 | 11/2014 | Kudavelly et al. | |
| 2015/0238259 A1 | 8/2015 | Albeck et al. | |
| 2015/0257847 A1 | 9/2015 | Higgins et al. | |
| 2016/0117857 A1 | 4/2016 | State et al. | |
| 2016/0166334 A1 | 6/2016 | Razzaque | |
| 2016/0166336 A1 | 6/2016 | Razzaque | |
| 2016/0196694 A1 | 7/2016 | Lindeman | |
| 2016/0270862 A1 | 9/2016 | Fuchs et al. | |
| 2016/0354152 A1 | 12/2016 | Beck | |
| 2017/0024903 A1 | 1/2017 | Razzaque | |
| 2017/0065352 A1 | 3/2017 | Razzaque | |
| 2017/0099479 A1 | 4/2017 | Browd et al. | |
| 2017/0128139 A1 | 5/2017 | Razzaque et al. | |
| 2017/0348067 A1 | 12/2017 | Krimsky | |
| 2018/0116731 A1 | 5/2018 | State et al. | |
| 2018/0263713 A1 | 9/2018 | State | |
| 2018/0289344 A1 | 10/2018 | Green et al. | |
| 2019/0021681 A1 | 1/2019 | Kohli | |
| 2019/0060001 A1 | 2/2019 | Kohli et al. | |
| 2019/0167354 A1 | 6/2019 | Heaney et al. | |
| 2019/0180411 A1 | 6/2019 | Keller | |
| 2019/0216547 A1 | 7/2019 | Heaney et al. | |
| 2019/0223958 A1 | 7/2019 | Kohli | |
| 2019/0247130 A1 | 8/2019 | State | |
| 2020/0046315 A1 | 2/2020 | State | |
| 2021/0027418 A1 | 1/2021 | Keller | |
| 2021/0113273 A1 | 4/2021 | State | |
| 2021/0161600 A1 | 6/2021 | Heaney | |
| 2021/0161601 A1 | 6/2021 | State | |

FOREIGN PATENT DOCUMENTS

| | | |
|---|---|---|
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |
| WO | WO 18/080844 | 5/2018 |

OTHER PUBLICATIONS

U.S. Appl. No. 15/041,868 including its ongoing prosecution history, including without limitation Office Actions, Amendments, Remarks, and any other potentially relevant documents, dated Feb. 11, 2016, Fuchs et al.

U.S. Appl. No. 15/068,323 including its ongoing prosecution history, including without limitation Office Actions, Amendments, Remarks, and any other potentially relevant documents, dated Mar. 11, 2016, Razzaque et al.

U.S. Appl. No. 15/415,398 including its ongoing prosecution history, including without limitation Office Actions, Amendments, Remarks, and any other potentially relevant documents, dated Jan. 25, 2017, State et al.

U.S. Appl. No. 15/598,616 including its ongoing prosecution history, including without limitation Office Actions, Amendments, Remarks, and any other potentially relevant documents, dated May 18, 2017, Razzaque et al.

U.S. Appl. No. 15/799,639 including its ongoing prosecution history, including without limitation Office Actions, Amendments, Remarks, and any other potentially relevant documents, dated Oct. 31, 2017, Green et al.

U.S. Appl. No. 15/882,709 including its ongoing prosecution history, including without limitation Office Actions, Amendments, Remarks, and any other potentially relevant documents, dated Jan. 29, 2018, State et al.

U.S. Appl. No. 15/995,059 including its ongoing prosecution history, including without limitation Office Actions, Amendments, Remarks, and any other potentially relevant documents, dated Apr. 17, 2018, Kohli et al.

U.S. Appl. No. 16/052,289, including its ongoing prosecution history, including without limitation Office Actions, Amendments, Remarks, and any other potentially relevant documents, dated Aug. 1, 2018, Kohli et al.

U.S. Appl. No. 16/178,002 including its ongoing prosecution history, including without limitation Office Actions, Amendments, Remarks, and any other potentially relevant documents, dated Nov. 1, 2018, Heaney et al.

U.S. Appl. No. 16/177,894 including its ongoing prosecution history, including without limitation Office Actions, Amendments, Remarks, and any other potentially relevant documents, dated Nov. 1, 2018, Keller et al.

U.S. Appl. No. 16/209,021 including its ongoing prosecution history, including without limitation Office Actions, Amendments, Remarks, and any other potentially relevant documents, dated Dec. 4, 2018, Razzaque et al.

U.S. Appl. No. 16/255,629 including its ongoing prosecution history, including without limitation Office Actions, Amendments, Remarks, and any other potentially relevant documents, dated Jan. 23, 2019, Kohli.

(56) References Cited

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.
"AIM 3D Needle Placement Software from InnerOptic", Medgadget, Sep. 21, 2012.
AIM Section 5: 510k Summary, submitted by InnerOptic Technology, Inc., in 5 pages, submission date May 17, 2012.
"Cancer Facts & Figures 2004," www.cancer.org/downloads/STT/CAFF_finalPWSecured.pdf, copyright 2004 American Cancer Society, Inc., printed Sep. 19, 2007, 60 pages.
Cancer Prevention & Early Detection Facts & Figures 2004; National Center for Tobacco-Free Kids; 2004; American Cancer Society; USA.
"David Laserscanner <-Latest News <-Institute for Robotics and Process Control <-Te . . . ," http://www/rob.cs.tu-bs.de/en/news/david, printed Sep. 19, 2007, 1 page.
"InnerOptic's AIM System Receives DA 510(K) Clearance", InnerOptic Technology, Inc., Sep. 18, 2012.
"Laser scanned 3d model Final" video, still image of video attached, http://www.youtube.com/watch?v+DaLgIgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth. php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 17 pages (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.

Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/lit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British: Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Fahey et al., "Meta-analysis of Pap Test Accuracy; American Journal of Epidemiology," 1995 141(7):680-689; The John Hopkins University School of Hygiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.
Fuchs, et al.: "Optimizing a Head-Tracked Stereo Display System to Guide Hepatic Tumor Ablation," Departments of Computer

(56) References Cited

OTHER PUBLICATIONS

Sciences and Radiology, and School of Medicine, University of North Carolina at Chapel Hill; InnerOptic Technology, Inc. 2008.
Fuchs, et al.: "Virtual Environments Technology to Aid Needle Biopsies of the Breast," Health Care in the Information Age, Ch. 6. pp. 60-61, Presented in San Diego, Jan. 17-20, 1996, published by IOS Press and Ohmsha Feb. 1996.
Fuhrmann A. et al., Comprehensive calibration and registration procedures for augmented reality; Proc. Eurographics Workshop on Virtual Environments 2001,219-228 (2001).
Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
StereoMirror Technology Webpage, http://www.planar.com/products/flatpanel_monitors/stereoscopic/ (Printed Dec. 29, 2011).
Herline et al., Surface Registration for Use in Interactive, Image-Guided Liver Surgery, Computer Aided Surgery 5:11-17 (2000).
Holloway, R.; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published no earlier than Mar. 1, 2008.
InVision User Manual; Professional instructions for Use, Published no earlier than Dec. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).
Kato, Amami, et al., A frameless, armless navigational system for computer-assisted neurosurgery, Journal of Neurosurgery, vol. 74, No. 5, May 1991, pp. 845-849.
Keller et al., "What is it in Head Mounted Displays (MDs) that really make them all so terrible?," pp. 1-8 (1998).
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).

Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 (August), 1997: pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Unltrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
Ohnesorge, Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization arid Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.

(56) References Cited

OTHER PUBLICATIONS

Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of the International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, 10 pages (Aug. 1996).
State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT-Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
U.S. Appl. No. 16/920,560 including its ongoing prosecution history, including without limitation Office Actions, Amendments, Remarks, and any other potentially relevant documents, dated Jul. 1, 3020, Keller et al.
U.S. Appl. No. 16/985,580 including its ongoing prosecution history, including without limitation Office Actions, Amendments, Remarks, and any other potentially relevant documents, dated Aug. 5, 2020, State et al.
U.S. Appl. No. 17/071,256 including its ongoing prosecution history, including without limitation Office Actions, Amendments, Remarks, and any other potentially relevant documents, dated Oct. 15, 2020, Heaney et al.
U.S. Appl. No. 17/071,459 including its ongoing prosecution history, including without limitation Office Actions, Amendments, Remarks, and any other potentially relevant documents, dated Oct. 15, 2020, State et al.
Edwards et al., Video See-Through Design for Merging of Real and Virtual Environments, VRAIS '93, pp. 1-11 (1993).
Lipton, "Foundations of the Steroscopic Cinema A Study in Depth," Van Nostrad Reinhold Company, pp. 1-319 (1982).
Splechtna et al, Comprehensive calibration and registration procedures for augmented reality; Proc. Eurographics Workshop on Virtual Environments 2001, 219-228 (2001).
U.S. Appl. No. 17/446,417 including its ongoing prosecution history, including without limitation Office Actions, Amendments, Remarks, and any other potentially relevant documents dated Aug. 30, 2021, Kohli et al.

* cited by examiner

LOUPE DISPLAY

CROSS-REFERENCE TO RELATED APPLICATIONS

The present application is a continuation of U.S. patent application Ser. No. 15/611,454, filed Jun. 1, 2017, entitled "Loupe Display," which is a continuation of U.S. patent application Ser. No. 15/199,630, filed Jun. 30, 2016, entitled "Loupe Display," which claims priority benefit to U.S. Provisional Application No. 62/296,440, filed Feb. 17, 2016, entitled "Loupe Display", each of which is hereby incorporated herein by reference in its entirety. Any and all applications for which a foreign or domestic priority claim is identified in the Application Data Sheet as filed with the present application are incorporated by reference under 37 CFR 1.57 and made a part of this specification.

BACKGROUND

Various systems are available to aid a healthcare provider to guide a medical device in a patient or to provide user viewing an object with additional information. The systems can provide image guidance cues to aid the healthcare provider or user, and can also provide additional information for the users benefit.

DETAILED DESCRIPTION

Figure 1A:
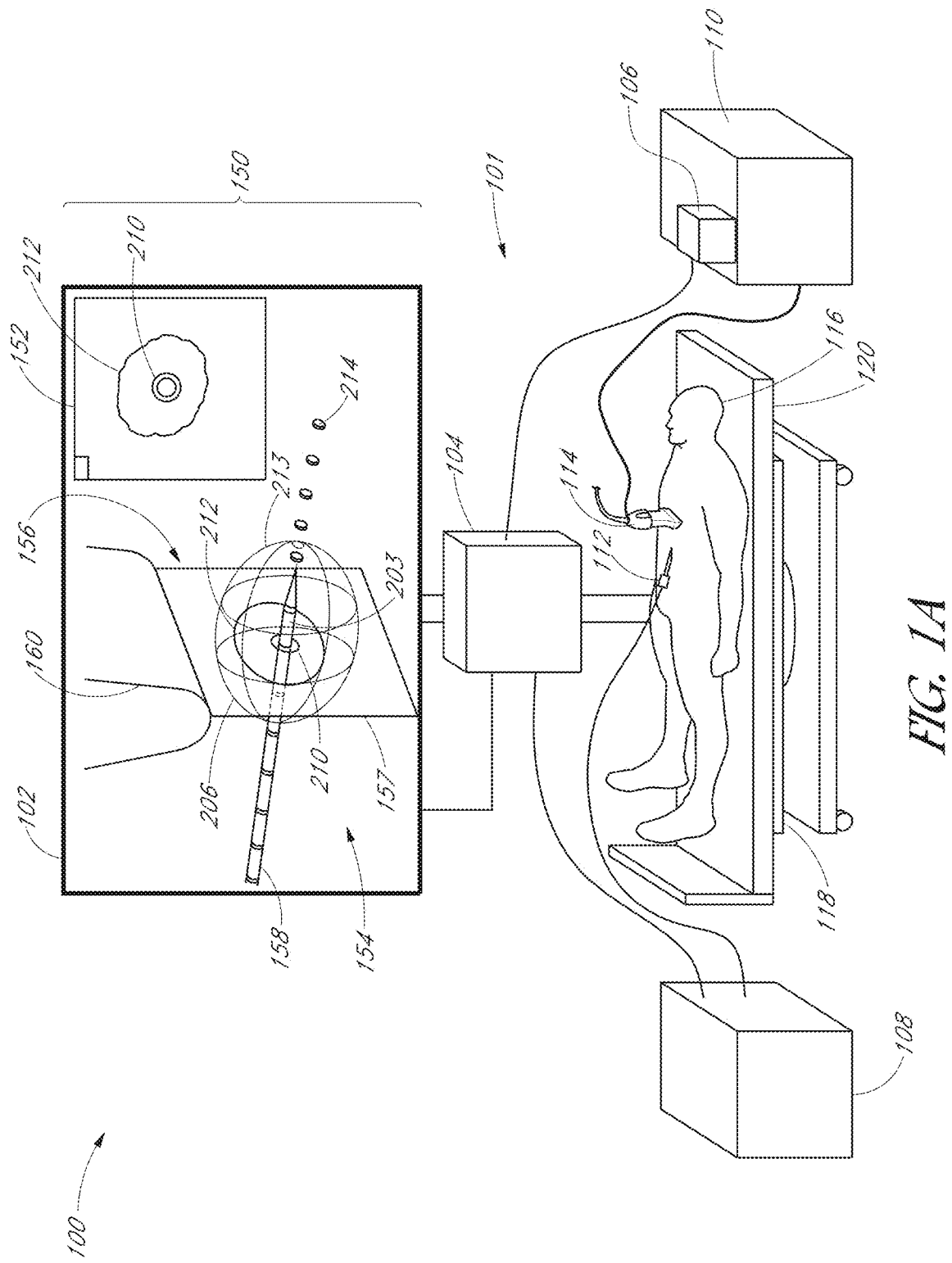
FIG. 1A is a diagram illustrating an embodiment of an environment for image-guided medical procedures.

Implementations disclosed herein provide systems, methods, and apparatus for generating images facilitating medical device insertion into tissue by an operator and other guidance tasks. Certain embodiments pertain to a free-hand medical device guidance system. The system can provide the healthcare provider manual control over the medical device, while making the spatial relationships between the target, medical device and U/S image more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled SYSTEMS, METHODS, APPARATUSES, AND COMPUTER-READABLE MEDIA FOR IMAGE MANAGEMENT IN IMAGE-GUIDED MEDICAL PROCEDURES; U.S. patent application Ser. No. 13/753,274, filed Jan. 29, 2013, entitled MULTIPLE MEDICAL DEVICE GUIDANCE (the '274 Application); U.S. patent application Ser. No. 14/212,933, filed Mar. 14, 2014, entitled MEDICAL DEVICE GUIDANCE; U.S. patent application Ser. No. 14/872,930, entitled AFFECTED REGION DISPLAY, filed Oct. 1, 2015; and U.S. patent application Ser. No. 14/968,445, filed Dec. 14, 2015, entitled SURGICAL GUIDANCE INTERSECTION DISPLAY; each of which is hereby incorporated herein by reference in its entirety.

The system can aid a healthcare provider in guiding one or more medical devices through the tissue of the patient and/or placing the medical devices, and can be used for treatment of tumors, fibroids or cysts, with bipolar radiofrequency medical device ablation, multiple microwave medical devices, electroporation, and/or electrochemotherapy systems, etc. It can also be used for nerve or muscle stimulation or sensing (electrodes in the spine, brain). The system can be used during open surgery, laparoscopic surgery, endoscopic procedures, biopsies, and/or interventional radiology procedures.

The system can be used in conjunction with live intraoperative ultrasound (U/S), pre-operative or intra-operative CT, or any cross-sectional medical imaging modality (e.g. MRI, OCT, etc.). In addition, the system can use a variety of techniques to determine the position and/or orientation of one or more medical devices. For example, the system can use the NDI Aurora magnetic system, the Ascension MedSafe system, NDI Polaris optical system, etc. In some embodiments, a position sensor can be embedded inside, or affixed to each medical device, at the tip, along the shaft, and/or on the handle. Sensors can be built into the medical devices or attached after manufacturing, as described in greater detail in U.S. application Ser. No. 14/212,184, filed Mar. 14, 2014, entitled SENSOR MOUNT, incorporated herein in its entirety.

Each medical device can be associated with one or more sensors, which can continually, or repeatedly, report position and/or orientation, or a single sensor can be used for all the medical devices. In embodiments where one sensor is used, the healthcare provider can attach the sensor to the particular medical device that she is intentionally repositioning, and then, once she has placed that medical device, she can remove the sensor and attach it to the next medical device she is repositioning. In some embodiments, the medical devices can be manipulated by the healthcare provider. In certain embodiments, the system can be used with a robotic manipulator, where the robot controls the medical devices.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator.

Image Guidance Systems

FIG. 1A is a diagram illustrating an embodiment of an environment 100 for image-guided medical procedures. In the illustrated embodiment, the environment 100 includes a display 102 displaying an image 150, an image guidance unit 104, a position sensing unit 106, a surgical system 108, imager 110, medical devices 112, 114, a patient 116, a stand 118, and a table 120. In some embodiments, an image guidance system 101 can include any one or any combination of the display 102, the image guidance unit 104, the position sensing unit 106, the surgical system 108, the imager 110, the medical devices 112, 114, the stand 118, and/or the table 120.

In some embodiments, the position sensing unit 106 can track medical devices 112, 114 within an area or volume, which can also be referred to as a tracked region or position sensing region, and provide data to the image guidance unit 104. The medical devices 112, 114 can include invasive medical devices, such as, but not limited to, biopsy needles, ablation needles, surgical needles, nerve-block needles, or other needles, electrocautery device, catheters, stents, laparoscopes or laparoscopic cameras, ultrasound transducers, or other instruments that enter a part of the body, and non-invasive medical devices that do not enter the body, such as, but not limited to, ultrasound transducers, probes, or other external imaging devices, etc. The medical devices 112, 114 can also include medical imaging devices that provide or aid in the selection or generation of medical images for display. In some embodiments, the medical imaging device can be any device that is used to select a particular medical image for display or generate medical images. The medical imaging devices can include invasive medical devices, such as laparoscopic cameras or invasive ultrasound transducers, and non-invasive medical devices, such as external ultrasound transducers.

Although only two medical devices 112, 114 are shown in FIG. 1A, it will be understood that additional medical devices can be tracked and associated data can be provided to the image guidance unit 104. The image guidance unit 104 can process or combine the data and show image guidance data on display 102. This image guidance data can be used by a healthcare provider to guide a procedure and improve care. There are numerous other possible embodiments of system 101. For example, many of the depicted components can be joined together to form a single component and can be implemented in a single computer or machine. Further, additional position sensing units can be used in conjunction with position sensing unit 106 to track relevant medical devices 112, 114, as discussed in more detail below. Additional imagers 110 can be included, and combined imaging data from the multiple imagers 110 can be processed by image guidance unit 104 and shown on display 102. Additionally, two or more surgical systems 108 can be used.

Information about and from multiple surgical systems 108 and attached medical devices 112 (and additional medical devices not shown) can be processed by image guidance unit 104 and shown on display 102. These and other possible embodiments are discussed in more detail below. It will be understood that any combination of the display objects, image guidance cues, etc., described herein can be displayed concurrently, or simultaneously. Further, reference to displaying objects "concurrently" and/or "simultaneously" is to be interpreted broadly and may refer to displaying objects in such a way that to a human observer the objects are visible at the same time.

Imager 110 can be communicatively coupled to image guidance unit 104. In some embodiments, imager 110 can be coupled to a second display unit (not shown). The second display unit can display imaging data from imager 110. The imaging data displayed on display 102 and displayed on second display unit can be the same or different. In some embodiments, the imager 110 can be an ultrasound machine 110, the medical device 114 can be a movable imaging unit, such as an ultrasound transducer 114 or ultrasound probe 114, and the second display unit can be a display associated with the ultrasound machine 110 that displays the ultrasound images from the ultrasound machine 110. In some embodiments, a movable imaging unit 114 can be communicatively coupled to image guidance unit 104. The movable imaging unit 114 can be useful for allowing a user to indicate what portions of a first set of imaging data are to be displayed. For example, the movable imaging unit 114 can be an ultrasound transducer 114, a needle or other medical device, for example, and can be used by a user to indicate what portions of imaging data, such as a pre-operative CT scan, to show on a display 102 as image 150. Further, in some embodiments, there can be a third set of pre-operative imaging data that can be displayed with the first set of imaging data.

In some embodiments, a navigation system 101 comprises a display 102 and a position sensing unit 106 communicatively coupled to image guidance unit 104. In some embodiments, position sensing unit 106, display 102, and image guidance unit 104 are coupled to the stand 118. Image guidance unit 104 can be used to produce images 150 that are displayed on display 102. The images 150 produced on display 102 by the image guidance unit 104 can be determined based on ultrasound or other visual images from the first medical device 112 and second medical device 114.

In the illustrated embodiment, the image 150 includes a 2D viewing area 152 and a 3D viewing area 154 (which can also be referred to as a virtual 3D space) each of which includes various display objects. In the 2D viewing area, some or all of the display objects can be displayed as 2D objects. However, it will be understood that some of the display objects in the 2D viewing area can be displayed as 3D objects. In the 3D viewing area 154, some or all of the display objects are displayed as 3D objects. Furthermore, the display objects in the 3D viewing area can be displayed in a perspective based at least in part on a point-of-view location. In the illustrated embodiment, the display objects include an image region 156 with an image or image slice 157, a virtual medical device 158 corresponding to the first medical device 112, a virtual imaging device 160 corresponding to the second medical device 114, trajectory indicator 164, and affected region indicator 206. It will be understood that any combination of the aforementioned display objects can be displayed in the 2D viewing area and/or 3D viewing area as desired.

As a non-limiting example, if the first medical device 112 is an ablation needle 112 and the second medical device 114 is an ultrasound probe 114, then images 150 produced on display 102 can include the images, or video, from the ultrasound probe 114 (non-limiting example: image slice 157) combined with other medical display objects and image guidance cues, such as projected medical device drive (non-limiting example: trajectory indicators 164) or projected ablation volume 213, determined based on the emplacement of ablation needle 112. If the first medical device 112 is an ultrasound probe 112 and the second medical device 114 is a laparoscopic camera 114, then images 150 produced on display 102 can include the video stream from the laparoscopic camera 114 combined with ultrasound data superimposed on the laparoscopic image. More medical devices can be added to the system 101. For example, the system 101 can include an ultrasound probe, ablation needle, laparoscopic camera, stapler, cauterizer, scalpel and/or any other medical device or medical device. The system 101 can also process and/or display collected data, such as preoperative CT scans, X-Rays, MRIs, laser scanned 3D surfaces etc.

The term "emplacement" as used herein is a broad term and may refer to, without limitation, position and/or orientation or any other appropriate location information. The term "pose" as used herein is a broad term encompassing its plain and ordinary meaning and may refer to, without limitation, position and orientation or any other appropriate location information. In some embodiments, the imaging data obtained from one or both of medical devices 112 and 114 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, medical devices 112 and 114 can also be scalpels, implantable hardware, or any other device used in surgery. Any appropriate surgical system 108 or imager 110 can be communicatively coupled to the corresponding medical instruments 112 and 114.

As noted above, the images 150 produced can also be generated based on live, intraoperative, or real-time data obtained using the second medical device 114, which is communicatively coupled to imager 110. The term "real-time" as used herein is a broad term and has its ordinary and customary meaning, including without limitation instantaneously or nearly instantaneously. The use of the term real-time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

The medical devices 112, 114 can be communicatively coupled to the position sensing unit 106 (non-limiting example: sensors embedded or coupled to the medical devices 112, 114 can be communicatively coupled with the position sensing unit 106). The position sensing unit 106 can be part of imager 110 or it can be separate. The position sensing unit 106 can be used to determine the emplacement of first medical device 112 and/or the second medical device 114. In some embodiments, the position sensing unit 106 can include a magnetic tracker and/or one or more magnetic coils can be coupled to medical devices 112 and/or 114. In some embodiments, the position sensing unit 106 can include an optical tracker and/or one or more visually-detectable fiducials can be coupled to medical devices 112 and/or 114. In some embodiments, the position sensing unit 106 can be located below the patient. In such embodiments, the position sensing unit 106 can be located on or below the table 120. For example, in embodiments where the position sensing unit 106 is a magnetic tracker, it can be mounted below the surgical table 120. Such an arrangement can be useful when the tracking volume of the position sensing unit 106 is dependent on the location of the position sensing unit 106, as with many magnetic trackers. In some embodiments, magnetic tracking coils can be mounted in or on the medical devices 112 and 114.

In some embodiments, the position sensing unit can determine one or more x, y, z coordinates and/or the quaternions (non-limiting examples: yaw, pitch, and/or roll) of tracking sensors associated with one or more of the medical devices 112, 114. In certain cases, the position sensing unit can determine the one or more x, y, z coordinates of the tracking sensors with respect to a position sensing coordinate system, as described in greater detail below. In some embodiments, the position sensing unit 106 can be an electromagnetic measurement system (non-limiting example: NDI Aurora system) using sensor coils for tracking sensors attached to the first and/or second medical devices 112, 114. In some embodiments, the position sensing unit 106 can be an optical 3D tracking system using fiducials for tracking sensors. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron Micron-Tracker2. In some embodiments, the position sensing unit 106 can each be an inertial 3D tracking system comprising a compass, accelerometer, tilt sensor, and/or gyro, such as the InterSense InertiaCube or the Nintendo Wii controller, mechanical tracking system, camera-based tracking system, radar-based tracking system, etc. In some embodiments, the position sensing unit 106 can be attached to or affixed on the corresponding medical device 112 and 114.

In some embodiments, the position sensing units 106, can include sensing devices such as the HiB all tracking system, a GPS device, or signal emitting device that would allow for tracking of the position and/or orientation (non-limiting example: emplacement) of the tracking sensor (also referred to as an emplacement sensor). In some embodiments, a position sensing unit 106 can be affixed to either or both of the medical devices 112, 114. The medical devices 112 or 114 can be tracked by the position sensing unit 106. A room coordinate system reference, such as the display 102 can also be tracked by the position sensing unit 106 in order to determine the emplacements of the medical devices 112, 114 with respect to the room coordinate system. Devices 112, 114 can also include or have coupled thereto one or more accelerometers, which can be used to estimate movement, position, and location of the devices. In some embodiments, the position sensing unit 106 can be an Ascension Flock of Birds, Nest of Birds, driveBAY, medSAFE, trakSTAR, mini-BIRD, MotionSTAR, pciBIRD, or Calypso 2D Localization System and tracking sensors attached to the first and/or second medical devices 112, 114 can be magnetic tracking coils.

The term "tracking sensor" (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below, or other sensors, such as accelerometers, gyroscopes, etc. In some embodiments, the tracking sensors can be implemented using optical position sensing devices, such as the HiBall tracking system and the position sensing unit 106 can form part of the HiB all tracking system. Tracking sensors can also include a GPS device or signal emitting device that allows for tracking of the position and/or orientation of the tracking sensor. In some embodiments, a signal emitting device might include a radio-frequency identifier (RFID). In such embodiments, the position sensing unit 106 can use the GPS coordinates of the tracking sensors or can, for example, triangulate the radio frequency signal being emitted by the RFID associated with tracking sensors. The tracking systems can also include one or more 3D mice. Furthermore, the system 101 can use the emplacement data associated with the tracking sensors (non-limiting example: received from the tracking sensors or from the position sensing unit 106) to determine other emplacement information, including, but not limited to the emplacement of a trajectory, an image plane, image region, imaged region, and/or one or more intersections, etc. In some cases, the tracking sensors can output the emplacement data, which can be used by the tracker to determine the emplacement of the tracking sensor. In certain cases, the tracker tracking the tracker sensors determines the emplacement of the tracking sensors without data being output from the tracking sensors. The determined emplacement information can be used to generate and display various image guidance cues, such as, but not limited to, the intersection indicator 210, the trajectory indicator 164, a variance volume, a shaded region, the image region 156 with the image slice 157, etc.

In some embodiments, the imaged region can correspond to the tissue or region that is imaged (area and/or volume) by the medical device 114. In some cases, the image plane can correspond to the plane at which the medical device 114 acquires an image and/or a plane in the virtual 3D space that is associated therewith. In certain cases, the image region can correspond to the region (area and/or volume) at which the medical device 114 acquires an image and/or to a region in the virtual 3D space associated therewith. For example, in some cases, image data acquired by the medical device 114 in the medical device's image region can be mapped to a corresponding virtual image region in the virtual 3D space. The image region may also be referred to as an image slice and/or image slab. Furthermore, in some embodiments, the image region can include at least a portion of the image plane.

The emplacement of the image plane, image region (area and/or volume), and/or imaged region can also be determined based at least in part on the operating parameters of the medical device 114. For example, the operating parameters can indicate what portion of the medical device 114 will capture an image (non-limiting example: emit ultrasonic waves), as well as the dimensions of the image region and/or imaged region (non-limiting examples: height, width, and/or depth of the image that will be acquired), as well as the image region.

Images 150 can be produced based on intraoperative or real-time data obtained using first medical device 112, which is coupled to first surgical system 108. In the illustrated embodiment of FIG. 1A, the first surgical system 108 is shown as coupled to image guidance unit 104. The coupling between the first surgical system 108 and image guidance unit 104 may not be present in all embodiments. In some embodiments, the coupling between first surgical system 108 and image guidance unit 104 can be included where information about first medical device 112 available to first surgical system 108 is useful for the processing performed by image guidance unit 104. For example, in some embodiments, the first medical device 112 can be an ablation needle 112 and first surgical system 108 can be an ablation system 108. In some embodiments, it can be useful to send a signal about the relative strength of planned ablation from ablation system 108 to image guidance unit 104 so that the image guidance unit 104 can show a predicted ablation volume 213. In other embodiments, the first surgical system 108 is not coupled to image guidance unit 104. Example embodiments including images and graphics that can be displayed are included below.

In some embodiments, the display 102 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 102 can be an alternating row or alternating column display. Example alternating row displays include the Miracube G240S, as well as Zalman Trimon Monitors. Alternating column displays include devices manufactured by Sharp, as well as many "auto-stereoscopic" displays (non-limiting example: Philips). In some embodiments, Sony Panasonic 3D passive displays and LG, Samsung, and/or Vizio 3D TVs can be used as well. Display 102 can also be a cathode ray tube. Cathode Ray Tube (CRT) based devices, can use temporal sequencing, showing imagery for the left and right eye in temporal sequential alternation. This method can also be used by projection-based devices, as well as by liquid crystal display (LCD) devices, light emitting diode (LED) devices, organic LED (OLED) devices, liquid crystal on silicon (LCOS) devices, DLP devices, virtual retinal display (MicroVision) devices, or the like.

In certain embodiments, the display 102 can be a head mounted display (HMD) worn by the user in order to receive 3D images from the image guidance unit 104. In such embodiments, a separate display, such as the pictured display 102, can be omitted. The 3D graphics can be produced using underlying data models, stored in the image guidance unit 104 and projected onto one or more 2D planes in order to create left and right eye images for a head mount, lenticular, or other 3D display. The underlying 3D model can be updated based on the relative emplacements of the various devices 112 and 114, as determined by the position sensing unit(s) 106, and/or based on new data associated with the devices 112 and 114. For example, if the second medical device 114 is an ultrasound probe, then the underlying data model can be updated to reflect the most recent ultrasound image. If the first medical device 112 is an ablation needle, then the underlying model can be updated to reflect any changes related to the needle, such as power or duration information. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more components, units, devices, or elements of various embodiments can be packaged and/or distributed as part of a kit. For example, in one embodiment, an ablation needle, one or more tracking sensors, 3D viewing glasses, and/or a portion of an ultrasound wand can form a kit. Other embodiments can have different elements or combinations of elements grouped and/or packaged together. Kits can be sold or distributed separately from or with the other portions of the system 101.

One will readily recognize that there are numerous other examples of image guidance systems 101 which can use, incorporate, support, or provide for the techniques, methods, processes, and systems described herein.

Depicting Medical Devices

It can often be difficult to discern the content of a 3D scene from a 2D depiction of it, or even from a 3D depiction of it. Therefore, various embodiments herein provide image guidance that can help the healthcare provider better understand the scene, relative emplacements or poses of objects in the scene and thereby provide improved image guidance.

With continued reference to FIG. 1A, the display 102 shows a perspective view of a virtual rendering 158 of medical devices 158, 160 being displayed on the display 102 with a perspective view of an image slice 157. The virtual medical devices 158, 160 can be displayed in a virtual 3D space with the display 102 acting as a window into the virtual 3D space. Thus, as a medical device 112 is moved to the right with respect to a point-of-view location (non-limiting example: the location of the point-of-view for viewing the 3D space), the virtual medical device 158 can also move to the right. Similarly, if the medical device 112 is rotated 90° so that the tip of the medical device is pointing away from the point-of-view location (non-limiting example: at the display 102), the virtual medical device 158 will likewise show the change in orientation, and show the tip of the virtual medical device 158 in the background and the other end of the virtual medical device 158 in the foreground. In some embodiments, as described in greater detail in U.S. application Ser. No. 14/212,933, incorporated herein by reference in its entirety, the point-of-view location can be a fixed location, such as a predetermined distance/angle from the display 102 or stand 118 and or a location configured by the user; or the point-of-view location can by dynamic. For example, the system 101 can track a user in real-time and determine the point-of-view location based at least in part on the tracked location of the user.

Some models of medical devices have markings such as bands around the shaft (to indicate distance along the shaft), and a colored region 203 near the tip to indicate from where the radio frequency or microwave energy is emitted in the case of an ablation probe. Healthcare providers performing medical device procedures are often familiar with these markings and can use them to help understand the spatial relationship between the medical device and anatomy. In some embodiments, the make and model of the medical device 112 is known to the image guidance system 101 and the virtual medical device 158 displayed in display 102 can resemble medical device 112. The features of medical devices that can be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system 101, can be a system default, can be detected by a camera or other device, can be received as data from an attached medical device, such as surgical system 108, or the information can be received in any other appropriate manner. Displaying on display 102, a virtual medical device 158 that resembles the medical device 112 can help healthcare providers associate the image guidance data with the real world and can provide more familiar guidance information to a healthcare provider, thereby further aiding the healthcare provider in the guidance task. For example, the healthcare provider can see the familiar markings on the medical device 158 being displayed on the display 102 and therefore be familiar with the distance and relative placement of the displayed medical device 158 with respect to other data, such as a tumor 212 or ablation volume 213 seen in a rendered ultrasound image slice 152, 157. This knowledge of relative placement of items being displayed can help the healthcare provider move the medical device 112 into place.

Consider an embodiment in which the virtual medical device 158 in the display 102 is an ablation needle depicting the portion of the needle that will perform the ablation, for example, the portion that emits the radio or microwave energy. If the display 102 also includes ultrasound data, then the doctor can be able to find the tumor 212 she wishes to ablate by moving the ultrasound probe around until she spots the tumor 212. In various embodiments, she will be able to see the displayed ultrasound data and its location relative to the displayed medical device with the markings. She can then drive the medical device until she sees, on display 102, that the emitter-portion of the medical device encompasses the tumor in the ultrasound, also seen on display 102. When she activates the ablation, she can then be more certain that she has ablated the correct portion of the tissue. Various embodiments of this are discussed below.

It will be understood that an image slice or image slab can also refer to image data received from an imaging device, such as an ultrasound transponder. In some embodiments, the image data can correspond to a cross-section of tissue having a certain thickness. In some instances, the imaging device can compact the image data, and/or treat the image data as 2D data, such that there is no perceived thickness. In certain embodiments, when the image slice is displayed in a 3D view, the system 101 can treat the image slice as a 2D or quasi 2D object. In such embodiments, the system 101 can cause the image slice to have little to no perceptible thickness. Accordingly, in certain embodiments, when the image slice is oriented orthogonally or perpendicularly with respect to the point-of-view location (or point-of-view plane), the system 101 can cause the display to display nothing or a line having a relatively small thickness, such as a few pixels, etc. In some cases, the number of pixels used to display the relatively small thickness of the image slice can correspond to the size of the display. For example, more pixels can be used for a larger display and fewer pixels can be used for a smaller display, etc.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic sheers, lasers (including CO$_2$ lasers), etc. For example, in various embodiments, the following devices can be tracked and various aspects of their design displayed on display 102: Olympus™ OES Pro Hystero-Resectoscope, SonoSurg Ultrasonic Surgical System Olympus™ GF-UC 160 Endoscope Wallus™ Embryo Transfer Catheter AngioDynamics.®. NanoKnife™, VenaCure™ laser, StarBurst, Uniblade, Habib.®. Resector Bovie™ Electrodes, Covidien Evident™, Cool-tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 102 that will allow her to know the relative pose, location, or emplacement of the tracked instrument(s) with respect to one another or with respect to imaging data and will be able to see, on display 220, the features of the instrument rendered in the scene.

Depicting Medical Device Placement, Trajectory, and Other Image Guidance Cues

In certain procedures, the system 101 can provide image prediction information related to the medical devices as image guidance cues. In the context of scalpel movement, this can be the location that the scalpel will hit if a healthcare provider continues to move the scalpel in a particular direction. In the context of ablation or biopsies, this can be the projected medical device placement if it is driven along its central axis, which is also referred to herein as a longitudinal axis.

FIG. 1A further illustrates an embodiment of a projected needle drive 164 (also referred to as a trajectory indicator) as an image guidance cue. If a healthcare provider is driving an ablation needle 112 into tissue, then she can know where the medical device will be driven. In some embodiments, the projected drive 164 of a medical device can be depicted on the display 102 and can show the healthcare provider the projected path 164 that the medical device 112 will take if it is driven along its central axis. Although the trajectory of only one medical device is displayed, it will be understood that the trajectory of multiple medical devices can be determined and displayed simultaneously on display 102, as described in greater detail in the '274 Application.

In some embodiments, to implement the trajectory indicators 164, the image guidance system 101 can draw a number of rings about the axis of the medical device shaft, extrapolated beyond its tip, as depicted in FIG. 1A. A healthcare provider can view and manipulate the emplacement of the medical device 112 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This can allow the healthcare provider to verify that the medical device 112 is properly aimed at the target and can drive the medical device 112 forward into the tissue such that it reaches its desired target or destination. For example, if the doctor identifies a tumor 212 in the ultrasound image, she can align the ablation needle 112 such that the drive projection rings on display 102 intersect or otherwise indicate that the medical device, if driven straight, will reach the tumor 212.

The rings can, in some embodiments, be spaced at regular (non-limiting examples: 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the drive speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device-shaft. This way, the user knows if the medical device is long enough to reach the target—even before the tip enters the patient. That is, in some embodiments, if the rings do not reach the target with the tip still outside the body, then the tip will not reach the target even when the entire length shaft is inserted into the body.

Other display markers can be used to show trajectory, such as a dashed, dotted, or solid line, transparent medical device shaft, point cloud, wire frame, etc. In some embodiments, three-dimensional rings can be used and provide depth cues and obscure little of the ultrasound image. Virtual rings or other virtual markers can be displayed semi-transparently, so that they obscure less of the ultrasound image than an opaque marker would.

Other prediction information can also be displayed as image guidance cues. For example, if a scalpel is being tracked by the image guidance system 101, then a cutting plane corresponding to the scalpel can be displayed (not pictured). Such a cutting plane can be coplanar with the blade of the scalpel and can project from the blade of the scalpel. For example, the projected cutting plane can show where the scalpel would cut if the doctor were to advance the scalpel. Similar prediction information can be estimable or determinable for cauterizers, lasers, and numerous other medical devices.

Furthermore, the data from two or more devices can be combined and displayed based on their relative emplacements or poses. For example, the rendered image slice 157 can be displayed on the image plane (non-limiting example: in the image region) with respect to the virtual medical device 158 on the display 102 in a manner that estimates the relative emplacements or poses of the medical imaging device 114 and the medical device 112. The image guidance cues associated with the virtual medical device 158, including the affected region indicator 206 and trajectory indicators 164, are shown spatially located with the rendered ultrasound image slice 157 on display 102.

In addition, the display 102 can include another image guidance cue in the form of an intersection indicator 210 that indicates where the virtual ablation medical device 158 (and/or its axis and/or its trajectory) intersects the ultrasound image slice 157. In some embodiments, the intersection indicator 210 can be displayed before the medical device is inserted, thereby allowing the healthcare provider to see where the medical device will intersect the image, or imaged region. As will be described in greater detail below, in some cases, due to uncertainties related to the emplacement of the medical devices, the system 101 can use a variance parameter to determine and display the intersection indicator 210.

In the illustrated embodiment, a tumor 212 appears in the ultrasound image, or rendered ultrasound image slice 157, and the virtual ablation needle 158 is shown driven through the tumor 212. As described in greater detail in U.S. application Ser. No. 14/872,930 (the '930 Application), incorporated herein by reference in its entirety, the displayed affected region (or affected region indicator) 206 can indicate what region or volume would be affected when the medical device 112 is operated. In the illustrated embodiment, the displayed affected region 206 can estimate where ablation would occur if the tissue were ablated at that time. As can be seen, in the illustrated embodiment, the displayed affected region 206 appears to cover the tumor displayed in the ultrasound image.

Various embodiments can include any combinations of the graphics described above and/or other graphics or image guidance cues. For example, in some embodiments, data related to a single medical device (such as an ablation needle, ultrasound probe, etc.) can be presented in more than one manner on a single display. Consider an embodiment in which device 112 is an ablation needle and device 114 is an ultrasound transducer. As mentioned previously, as the medical devices are displayed in a virtual 3D space, with the display 102 acting as a window into the virtual 3D space, if a healthcare provider orients medical imaging device 114 such that it is perpendicular to the point-of-view or point-of-view location (non-limiting example: perpendicular to the screen), the perspective view of the ultrasound image slice 157 would show only the edge and the contents of the ultrasound image slice 157 would not be visible. In some embodiments, the image guidance system 101 can track the healthcare provider's head using an emplacement sensor and/or a position sensing unit. In some embodiments, such as, when the head of a user is tracked, the healthcare provider can then move her head to the side, so that she sees the ultrasound image from a different point of view location.

In some embodiments, the image guidance system 101 can concurrently display a 2D view 152 of the ultrasound image with the 3D depiction 154, so that the ultrasound image is always visible, regardless of the emplacement in which the healthcare provider holds the medical imaging device 114. The 2D view 152 of the ultrasound data can be similar to what a healthcare provider is accustomed to seeing with traditional ultrasound displays. This can be useful to provide the healthcare provider with imaging to which she is accustomed and allows a healthcare provider to see the ultrasound data regardless of the then-current emplacement of the ultrasound probe with respect to the user.

In some embodiments, the 2D view 152 of an ultrasound image is depicted in the upper right corner of the monitor (though it can be placed in any location). In some embodiments, the guidance system 101 can automatically (and continually) choose a corner in which to render the 2D view 152 of the ultrasound image, based on the 3D position of the medical devices in the rendered scene. For example, ablation needle 112 can be held in the healthcare provider's left hand and the medical device shaft is to the left of the 3D view of the ultrasound image slice, so that the 2D view 152 of the ultrasound image in the upper right corner of display 102 does not cover any of the 3D features of the medical device (or vice-versa). If the medical device were held in the healthcare provider's right hand (and to the right of the ultrasound image slice 157, the virtual medical device shaft would appear on the right side. To prevent the 2D view 152 in the corner of display 102 from covering the medical device shaft, the system 101 can automatically move it to a corner that would not otherwise be occupied by graphics or data.

In some embodiments, the system 101 attempts to avoid having the 2D view 152 of the ultrasound image quickly moving among corners of the display in order to avoid overlapping with graphics and data in the display. For example, a function f can be used to determine which corner is most suitable for the 2D ultrasound image to be drawn in. The inputs to f can include the locations, in the screen coordinate system, of the displayed medical device tip, the corners of the 3D view of the ultrasound image, etc. In some embodiments, f s output for any given point in time is independent of fs output in the previous frames, which can cause the ultrasound image to move among corners of the display rapidly. In some embodiments, the image guidance system 101 will filter fs output over time. For example, the output of a filter g, for any given frame, could be the corner, which has been output by f the most number of times over the last n frames, possibly weighting the most recent values for f most heavily. The output of the filter g can be used to determine in which corner of display 102 to display the 2D ultrasound image and the temporal filtering provided by g can allow the 2D view 152 of the ultrasound image display to move more smoothly among the corners of the display 102.

In some embodiments, other appropriate virtual information and/or image guidance cues can be overlaid on the 2D view 152 of the ultrasound image as well as the 3D view 154. Examples include: an indication of the distance between the medical device's tip and the point in the plane of the ultrasound image that is closest to the medical device tip; the cross section or outline of the ablation volume that intersects with the ultrasound slice; and/or the intersection point, box, outline, etc. between the virtual medical device's axis and the ultrasound image plane.

Furthermore, it will be understood that other image guidance cues can be generated and displayed on the display as described in greater detail in the '274 Application, previously incorporated herein by reference. For example, the system 101 can generate and/or display graphical indicators that help indicate the spatial relationship between a medical device and an ultrasound image plane (non-limiting example: graphical image plane indicators) or other plane indicators to indicate the relative positions of the virtual medical device(s) and ultrasound image, features of interest, annotations, foundational plane indicators, foundational plane intersection indicators, other graphical indicators, approximate medical device location indicators, etc. As described in greater detail above and in the '274 Application, the various image guidance cues can be generated based at least in part on the emplacement information of the medical devices used with the system 101.

Figure 1B:
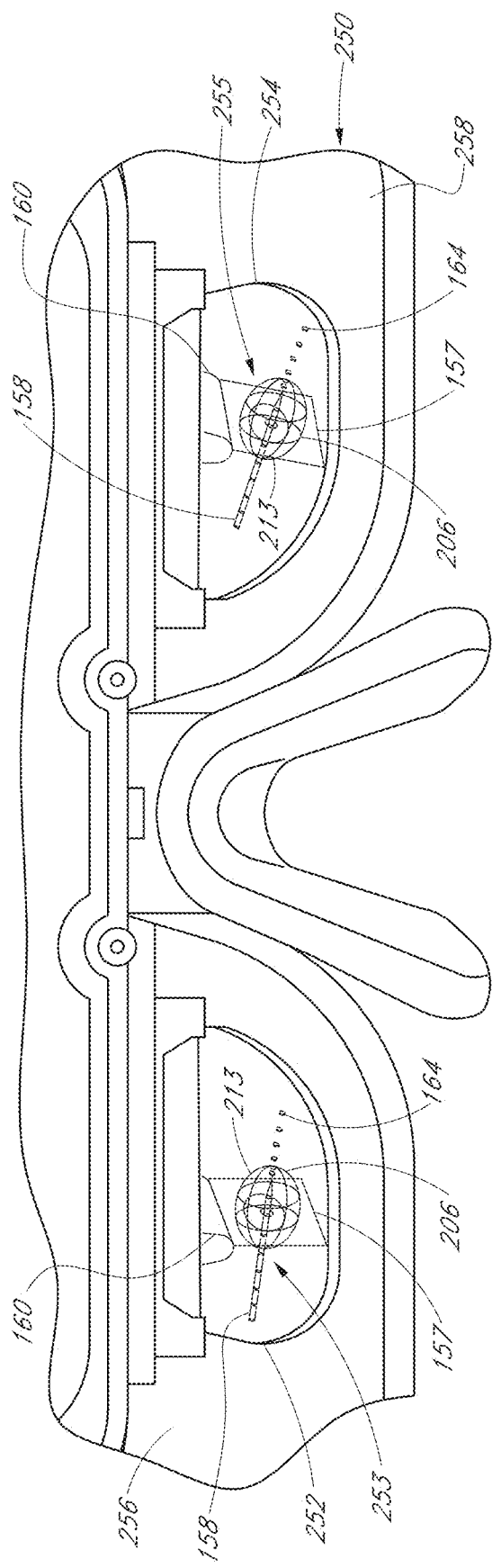
FIG. 1B is a diagram illustrating an embodiment of a rendering of image guidance cues and medical display objects on a head mounted display.
Figure 1B:
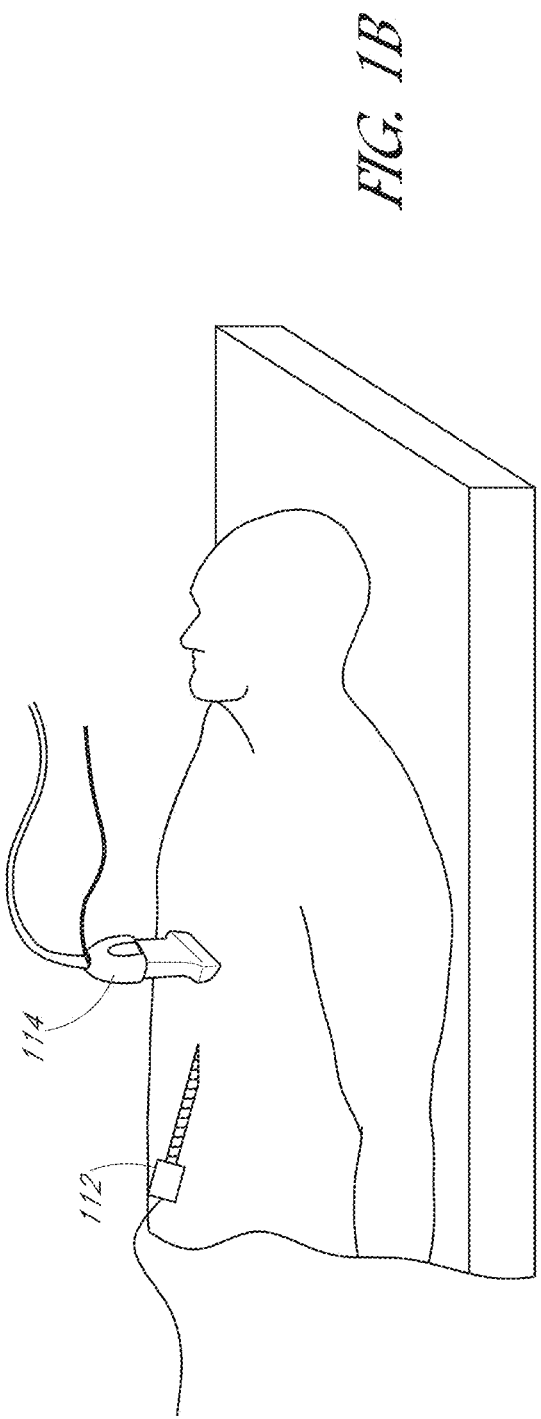

Referring now to FIG. 1B, virtual image content may be displayed on a head mounted display (HMD) 250 instead of or in addition to a display 102 as depicted in FIG. 1A. The HMD 250 may include one or more stereoscopic displays 252, 254 configured to display 3D content to a wearer of the HMD 250. For example, the HMD 250 can include a left stereoscopic display 252 configured to project visual content 253 to a left eye of a wearer, and a right stereoscopic display 254 configured to display visual content 255 to a right eye of a wearer. In some embodiments, displays 252, 254 can be opaque, and can be sized and located so as to occupy a subset of the field of view of a wearer. In certain embodiments, the displays 252, 254 can be transparent or translucent, or can be implemented as retinal scan displays that project an image onto the eye rather than display an image on the display screen.

Displays 252, 254 can allow the displayed content 253, 255 to be seen clearly without glare or interference due to light from the world in the region beyond the displays 252, 254. In certain embodiments, displays 252, 254 occupying less than the entire field of view of the wearer can allow the wearer to view the virtual content 253, 255 while also viewing the real environment in the portion of the wearer's field of view unoccupied by displays 252, 254, such as through transparent portions 256, 258 of the HMD 250.

In some embodiments, the imaging systems described herein can display virtual image content on the displays 252, 254 using a location offset with respect to the location of corresponding objects. For example, rather than displaying and/or augmenting content that is directly in front of the displays 252, 254 and/or the HMD 250, the displays 252, 254 can display and/or augment objects that are located elsewhere, such as below, above, or to the side of the displays 252, 254 and/or the HMD 250. In the illustrated embodiment, the virtual medical devices 158, 160 can be displayed with a vertical offset relative to the medical devices 112, 114 (or the position sensing region) so as to allow a wearer of the HMD 250, such as a surgeon, to simultaneously view the virtual medical devices 158, 160 on the displays 252, 254 and the patient 116 with real medical devices 112, 114 located below the HMD 250.

In certain embodiments, if the wearer rotates their head down or up, the display objects on the displays 252, 254 can shift up or down, respectively, relative to the displays 252, 254 (or the wearer's field of view). In some embodiments, the wearer rotates their head right or left, the displays 252, 254 can shift to the left or right, respectively, relative to the displays 252, 254 (or the wearer's field of view). Thus, the system 101 can cause the display objects in the displays 252, 254 to mimic the behavior of real objects located at a particular location at which a person is looking (or oriented), or offset from a particular location at which a person is looking (or oriented). Accordingly, in some embodiments, the system 101 can cause the displays 252, 254 to display display objects (non-limiting examples: virtual medical devices 158, 160) based at least in part on the emplacement of corresponding objects (non-limiting examples: medical devices 112, 114) relative to tracked displays 252, 254, or the emplacement of corresponding objects with an offset relative to tracked displays 252, 254.

The offset can be predetermined based on a dimension or preference of an individual wearer prior to use, or based on a default such as an average height or dimension of an expected wearer, or dynamic based on data received during use. An example offset can be a distance equal or approximately equal to the vertical distance between a wearer's elbow and the wearer's eye (non-limiting example: in the range of 0.5 m to 1 m), a measured distance between the HMD 250 and the medical devices 112, 114, etc. Non-limiting embodiments of methods for implementing the offset are described in greater detail with reference to FIGS. 5 and 6.

The HMD 250 can be implemented with any of the imaging systems described with reference to FIG. 1A. For example, displays 252, 254 can display virtual medical devices 158, 160 corresponding to real medical devices 112, 114. Displays 252, 254 can further display any other virtual image features described elsewhere herein, such as a medical image slice 157, trajectory 164, 2D viewing area 152, and/or affected region indicator 206.

Coordinate Systems

Figure 1C:
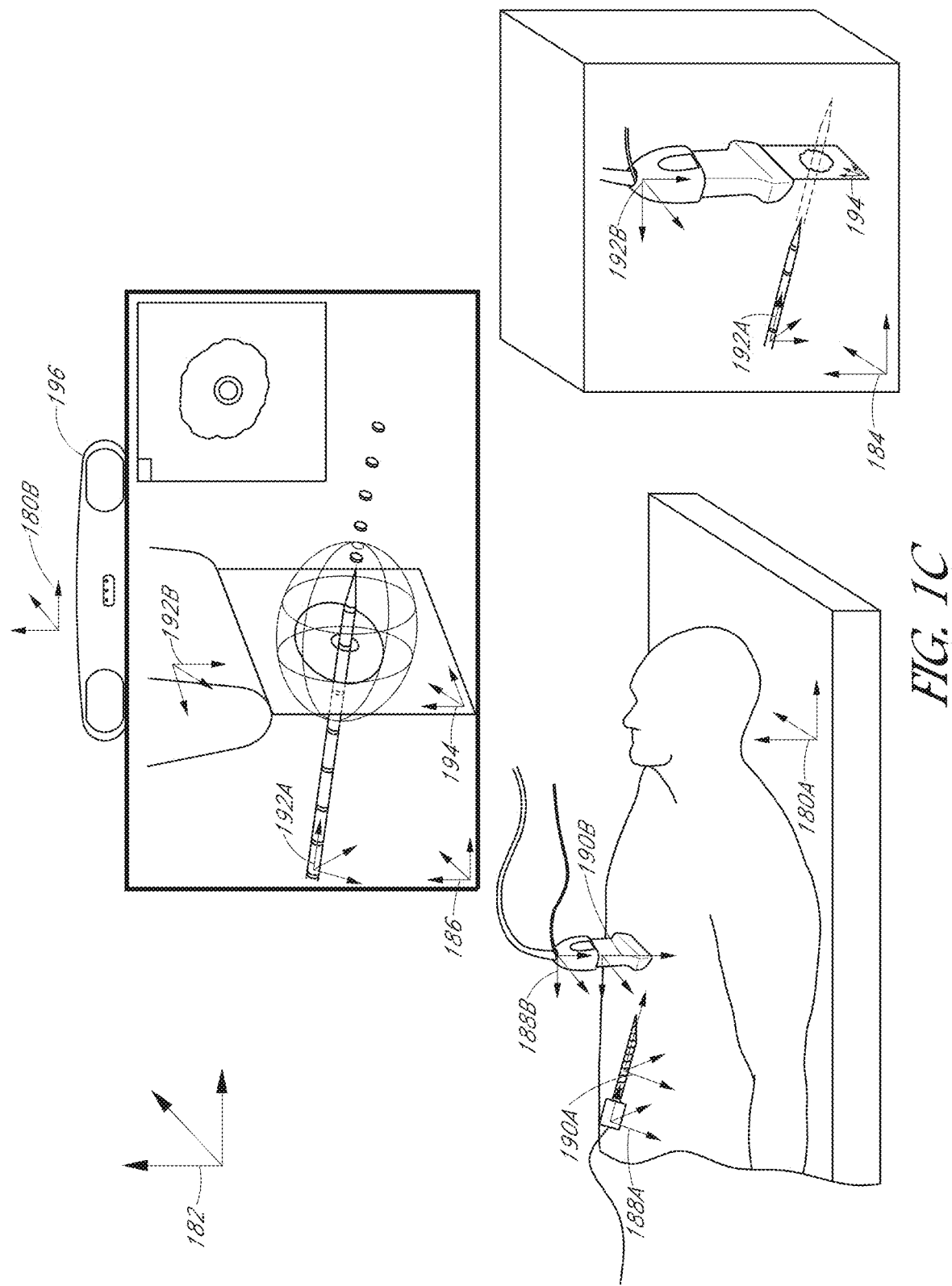
FIG. 1C is a diagram illustrating embodiments of coordinate systems that can be used by the system.

FIG. 1C is a diagram illustrating embodiments of coordinate systems that can be used by the system 101. The system 101 can the coordinate systems to track and display the various medical devices and images on the displays, including, but not limited to one or more position sensing coordinate systems 180A, 180B (generically referred to as 180), one or more room coordinate systems 182, one or more 3D scene coordinate systems 184, one or more display coordinate systems 186, one or more sensor coordinate systems 188A, 188B, one or more medical device coordinate systems 190A, 190B, one or more virtual medical device coordinate systems 192A, 192B, one or more medical image coordinate systems 194, etc.

A position sensing coordinate system 180 can be used to determine the emplacement of various objects within a position sensing region. For example, in some embodiments, the position sensing coordinate system 180 can refer to the coordinate system 180A used by a magnetic tracker (not shown) tracking objects within a magnetic field volume, or to the coordinate system 180B used by an optical tracker 196 tracking objects within a volume. In some cases, multiple position sensing coordinate systems 180 can be used together. For example, a magnetic position sensing coordinate system 180A can be used in conjunction with a magnetic tracker tracking sensor coils within a position sensing region that are coupled to medical devices and an optical position sensing coordinate system 180B can be used in conjunction with an optical tracker tracking a fiducial coupled to an HMD or a user, or to an optical tracker analyzing an image captured by an image sensor. It will be understood that any combination of the tracker systems and position sensing coordinate systems 180 can be used as desired. For example, in some cases, a single position sensing coordinate system 180 can be used to track tracking sensors associated with one or more medical devices and/or tracking sensors associated with a user or HMD. Similarly, a different position sensing coordinate system 180 can be used for each tracking sensor, or any combination thereof.

Room coordinate systems 182 can be used to determine the emplacement of objects within a room, such as an operating room. For example, the room coordinate system 182 can be used to determine or identify the relative emplacement of the position sensing unit, medical devices, tracking sensors, user, display, etc. relative to each other within a room.

A 3D scene coordinate system 184, which may also be referred to as a 3D volume or scene graph coordinate system, can be used to determine the emplacement of display objects within a virtual 3D scene. In some cases, the 3D scene coordinate system 184 can identify the relative emplacement of virtual objects within the 3D scene. In certain embodiments, the virtual objects can correspond to real objects, such as to medical devices 112, 114 and/or to computer-generated objects, such as such as trajectory cues 164, ablation volume 213, etc.

A display coordinate system 186 can be used to determine the emplacement of display objects for display on the display 102 and/or displays 252, 254. For example, the display coordinate system 186 can be used to determine the emplacement of virtual medical devices, medical image data streams, image guidance cues, and the like, within a display 102 and/or displays 252, 254. In some embodiments, the display coordinate system 186 can be used to determine how the objects within the 3D scene are to be displayed on the display 102 and/or displays 252, 254. For example, the display coordinate system 186 can be used to determine the point-of-view location, or eye point, relative to the 3D scene (or 3D volume coordinate system 184) or scene graph for viewing the contents of the 3D scene. As mentioned above, multiple display coordinate systems 186 can be used. For example, left-eye, right-eye, and/or center-eye display coordinate systems 186 can be used to display different perspective of the display objects within a 3D scene, such as when a 3D display and/or a HMD is being used.

A medical image coordinate system 194 can be used in conjunction with medical images used and/or processed by the system. As described previously, the medical images can be ultrasound images, CT image, MRI, images, etc. The images can be different sizes or shapes. For example, one ultrasound can output an image having one size and shape while a different ultrasound can output an image having a different size and/or shape. Similarly, CT, MRI, and ultrasound images may have different sizes and shapes. Accordingly, the medical image coordinate system can be used to identify the particular size and shape of the medical image being used and/or processed by the system 101.

It will be understood that fewer, more, or different coordinate systems can be used as desired. For example, in some embodiments, the 3D scene coordinate system 184 can be omitted or combined with display coordinate system 185 and/or the position sensing coordinate system 180. Furthermore, in some cases, one or more tracking sensor coordinate systems 188A, 188B, medical device coordinate systems 190A, 190B, virtual medical device coordinate systems 192A, 192B, or other objects etc., can have their own coordinate system. The coordinate systems for the tracking sensors, medical devices, and/or virtual medical devices can be used to identify the dimensions of the sensor/device/object and relationship of the sensor/device/object to other sensor/device/object or other coordinate systems. For example, a medical device coordinate system (or virtual medical device coordinate system) can identify the dimensions of a corresponding medical device or virtual medical device, as well as the emplacement of a tracking sensor relative to the medical device (or vice versa). Similarly, a medical imaging device coordinate system can identify the dimensions of the corresponding medical imaging device (or virtual medical imaging device) and/or an emplacement of a medical image relative to the medical imaging device (non-limiting example: the emplacement of an ultrasound image relative to the corresponding ultrasound transducer), or vice versa. The system 101 can use various coordinate systems to determine the emplacement of a portion or the entire object with respect to each other and with respect to the other coordinate systems.

The system 101 can use the various coordinate systems to determine emplacement of objects relative to each other and determine how to display the display objects on a display, such as the display 102 and/or the displays 252, 254. As a non-limiting example, to display a virtual rendering of an ultrasound transducer 160 and ultrasound image stream 157 on display 102 and/or displays 252, 254, the system 101 can determine the emplacement of a magnetic tracking sensor coupled to the ultrasound transducer 114 within a magnetic position sensing coordinate system 180. Using a magnetic tracking sensor coordinate system 188B, the system 101 can determine the location of each portion of the magnetic tracking sensor within the magnetic position sensing coordinate system 180. The system 101 can also determine the emplacement of each portion the ultrasound transducer 114 within the magnetic position sensing coordinate system by mapping the ultrasound transducer coordinate system 190B to the magnetic tracking sensor coordinate system 188B (or vice versa) and/or to the magnetic position sensing coordinate system 180.

In addition, the system 101 can map each portion of the ultrasound image 157 corresponding to the ultrasound transducer 114 to the magnetic position sensing coordinate system 180 by mapping an ultrasound image coordinate system 194 to the ultrasound transducer coordinate system 190B, the magnetic tracking sensor coordinate system 188B, and/or to the magnetic position sensing coordinate system 180.

To display the virtual ultrasound transducer 160 and ultrasound image slice 157, the system 101 can map the various objects from the magnetic position sensing coordinate system 180 to a room coordinate system 182, which can identify the relative emplacement of the position sensing coordinate system 180 to a display. The system can then map data to the 3D scene coordinate system 194 and/or the display coordinate system 186. For 3D viewing, the system 101 can map the objects to multiple display coordinate systems 186, such as left-eye and/or right-eye coordinate systems.

With continued reference to the non-limiting example, the system 101 can determine an emplacement of an optical tracking sensor corresponding to a user within an optical position sensing coordinate system 180B. The emplacement of the optical tracking sensor within the optical position sensing coordinate system 180B can be mapped to the room coordinate system 182, the 3D scene coordinate system 184, and/or the display coordinate systems 186 for display. In this way the system 101 can determine the emplacement of the ultrasound transducer 114 and ultrasound image slice 157 relative to the user and display a virtual rendering of the ultrasound transducer 160 and ultrasound image slice 157 within the 3D scene relative to the determined emplacement of the user.

Although the non-limiting example has been described as mapping the various objects and coordinate systems, to a position sensing coordinate system 180, the room coordinate system 182, the 3D scene coordinate system 184, and to display coordinate systems 186, it will be understood that the one or more of the objects or coordinate systems can be mapped directly or indirectly to any other coordinate system. For example, the medical device image can be mapped directly to a left-eye display coordinate system 186, etc. Thus, any of the real or virtual objects described herein may be represented, detected, or imaged in any coordinate system, and conversion between the various coordinate systems can be performed in components of the system such as image guidance unit 104, position sensing unit 106, imager 110, the HMD 250, or other components.

Furthermore, it will be understood that once the system 101 determines an emplacement of a medical device in one coordinate system, such as a position sensing coordinate system 180, the system 101 can determine the emplacement of a corresponding virtual medical device in a different coordinate system, such as the 3D scene coordinate system 184 or the screen coordinate system 186, by mapping the coordinates of the first coordinate system to the coordinates of the second coordinate system, or vice versa. Accordingly, references made herein to determining an emplacement of the medical device can also refer to determining an emplacement of a virtual medical device corresponding to the medical device, or vice versa. Similarly, references made herein to determining an emplacement of an object (non-limiting example: medical image) relative to the medical device can also refer to determining the emplacement of the object relative to a corresponding virtual medical device.

Head Mounted Display

Figure 2B:
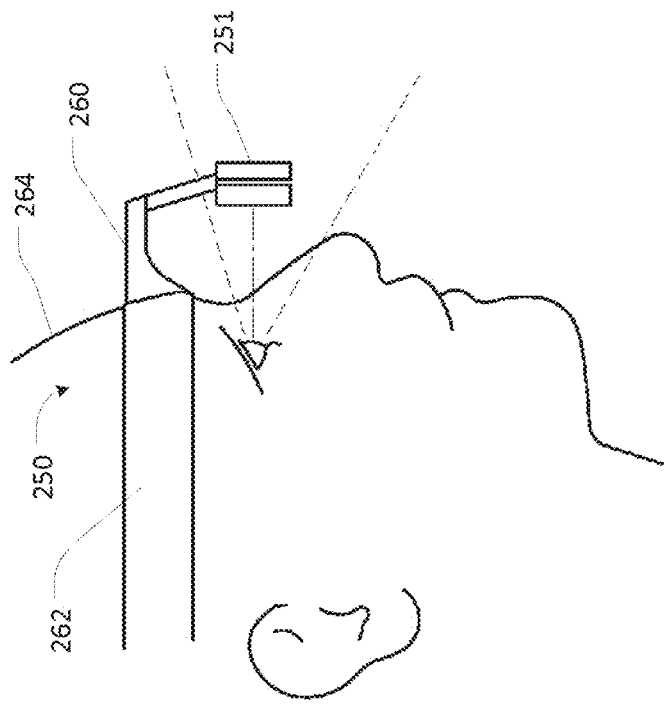
FIGS. 2A, 2B, and 2C are diagrams illustrating various embodiments of a head mounted display.
Figure 2A:
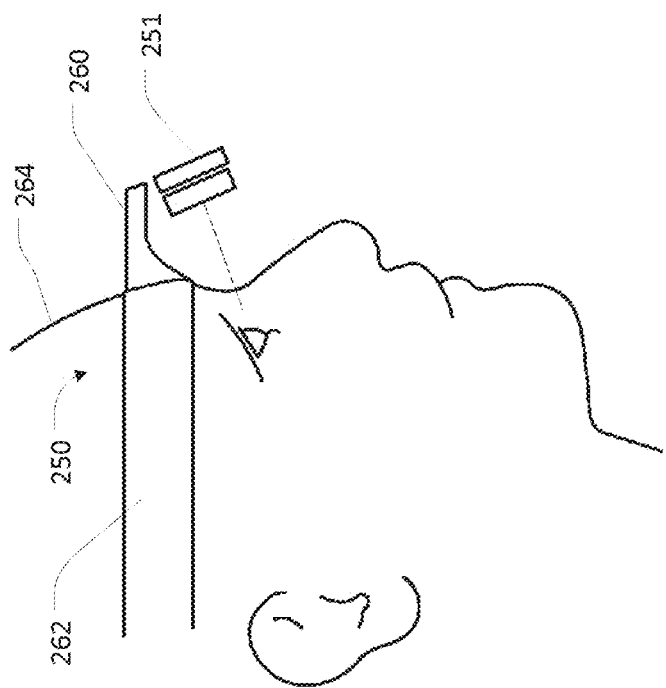
Figure 2C:
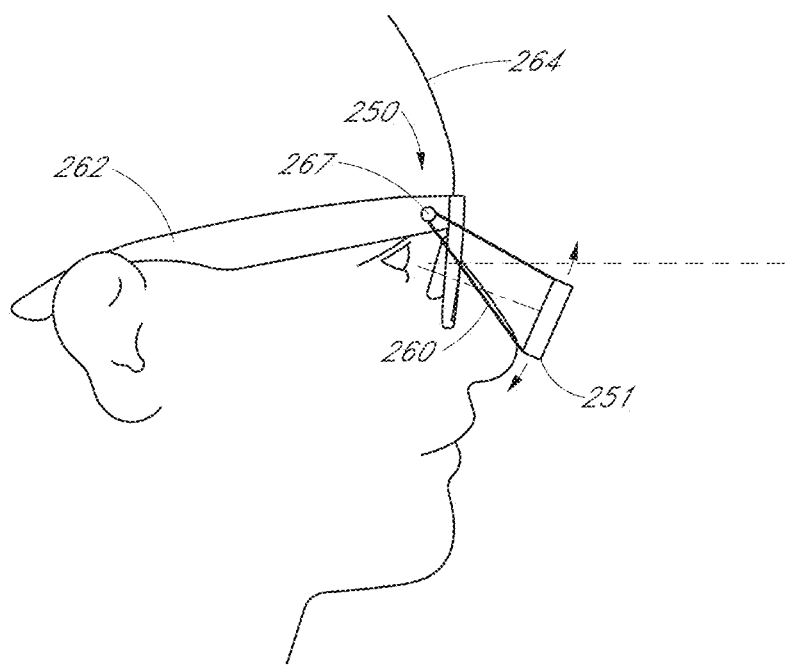

FIGS. 2A, 2B, and 2C are diagrams illustrating various embodiments of an HMD 250 configured for use with the system 101. In the illustrated embodiments of FIGS. 2A, 2B, and 2C, the HMD 250 can include left and/or right displays (generically referred to as display or displays 251) (only the right display is shown), a support structure 260 configured to support the displays 251 at a desired location, and a frame 262 configured to secure the display 251 and support structure 260 to the head of a wearer 264, such as a surgeon or other medical professional. Each display 251 can be centered laterally (non-limiting example: left to right) within the field of view of each eye of the wearer 264. The center of the display 251 can be located above eye level (as depicted in FIG. 2A), located at eye level, the location of the eye when a person is looking straight ahead irrespective of head orientation, or approximately eye level, such as ±15° from eye level (as depicted in FIG. 2B), or can be below eye level (as depicted in FIG. 2C).

In some embodiments, the HMD 250 can include fewer or more displays. For example, in some cases the HMD 250 can include one display. The single display can be configured for a left-eye view, right-eye view, monocular view, and/or can be centered with respect to the left eye, right eye, between the eyes, or some other location. Similarly, the HMD 250 could include more than two displays. For example, a third display could be used to display additional information, such as a non-perspective view of the ultrasound image, similar to 2D view 152 of FIG. 1A.

With respect to FIG. 2A, in some embodiments the display 251 can be vertically centered above eye level of the wearer 264 or vertically centered above the center of the orbit of the eye, causing the wearer 264 to look up to view the display. In some embodiments, the display 251 can be centered between >0° and ≤+30° from eye level. For example, the display 251 can be centered at, or approximately at 5°, 10°, 15°, 20°, 25°, or 30°, relative to eye level. However, it will be understood that the display 251 can be centered at >+30° from eye level. By centering the display above eye level, in some cases, a wearer 264 can have an unobstructed view of the environment located below the display 251 or HMD 250. In certain embodiments, the display 251 can be located (and sized) such that the wearer 264 has an unobstructed view of the environment at or below eye level. In some embodiments, the display 251 can be located such that the user has an unobstructed view of her hands when placed at or below the chest or when placed directly in front of the wearer at or below eye level.

With respect to FIG. 2B, in certain cases, the displays 251 can be vertically centered at eye level or approximately eye level. By centering the displays 251 at eye level or approximately eye level, a wearer 264 can view the displays 251 by looking straight ahead. In some cases, the wearer 264 can have an unobstructed view, relative to the HMD and/or display 251, of the environment above and below the portion of the field of view occupied by the displays 251. In addition, locating the displays 251 in the center of the field of view can prevent eye strain, fatigue, or other discomfort that can be caused by looking up or down for an extended time period. In some embodiments, the display 251 can be located (and sized) such that the user has an unobstructed view, relative to the HMD and/or display 251, of her hands when located at or below the chest, or below eye level, such as when working at a desk or on a surgical table. In certain embodiments, the display 251 can be located such that the user has an unobstructed view of her hands when located above eye level.

With respect to FIG. 2C, in some embodiments the display 251 can be vertically centered below eye level of the wearer 264 or vertically centered below the center of the orbit of the eye, causing the wearer 264 to look down to view the display. In some embodiments, the display 251 can be centered between <0° and ≥−45° from eye level. For example, the display 251 can be centered at, or approximately at −5°, −10°, −15°, −20°, −25°, −30°, −35°, −40°, or −45°, relative to eye level. However, it will be understood that the display 251 can be centered at <−45° from eye level. By centering the display below eye level, in some cases, a wearer 264 can have an unobstructed view, relative to the HMD and/or display 251, of the environment located above the display 251 or HMD 250. In certain embodiments, the display 251 can be located (and sized) such that the wearer 264 has an unobstructed view of the environment at or above eye level. In some embodiments, the display 251 can be located such that the user has an unobstructed view of her hands when placed at or above eye level.

In some embodiments, the support structure 260 can include one or more hinges, such as at locations 263, 265, or gear 267, to enable a wearer 264 to manually change the location of the display 251 within her field of view based on personal preference and/or comfort.

In various embodiments, the display 251 can be sized and/or located so as to occupy a desired portion of the wearer's field of view. A typical human field of view can span approximately 180°-200° (approximately 110° for each eye) horizontally and 135° vertically. In certain embodiments, the display 251 can occlude a portion of the field of view large enough to provide useful content to the viewer, but small enough to allow the wearer to view objects in the world around the wearer through the unoccluded space surrounding the display 251.

In certain embodiments, such as when the displays 251 are opaque, the display(s) 251 can occlude a region of between approximately 10°-50° horizontally, leaving at least 130° unoccluded horizontally. For example, the display(s) 251 can occlude approximately (±a few degrees) 10°, 15°, 20°, 25°, 30°, 35°, 40°, 45°, or 50° of a wearer's horizontal field of view. The field of view occluded by the display(s) can be centered with respect to the user's field of view, centered with respect to the right eye or left eye of the user, or not centered. In certain embodiments, the occluded field of view can be split up, such that one portion of the occluded field of view is centered over, or otherwise occludes, the left eye field of view and another portion of the occluded field of view is centered over, or otherwise occludes, the right eye field of view. In some embodiments, the display(s) 251 can occlude between approximately 35°-135° horizontally. However, it will be understood that other sizes can be used such that the display occludes <35° or >135° horizontally In addition, in some embodiments, the display(s) 251 can occlude between 14°-110° vertically, such that at least 25° are unoccluded vertically. For example, the display(s) 251 can occlude approximately (±a few degrees) 10°, 20°, 30°, 40°, 50°, 60°, 70°, 80°, 90°, 100°, or 110° of a wearer's vertical field of view. The field of view occluded by the display(s) can be centered with respect to eye level, centered below eye level, or centered above eye level. However, it will be understood that other sizes can be used such that the display occludes <14° or >110° vertically. In addition, it will be understood that the vertical size of the display(s) can be combined with any combination of the horizontal size of the displays.

It will be understood that the HMD 250 can include fewer, more, or different components as desired. For example, in some embodiments, the HMD 250 can the display(s) 251 can be attached directly to frame 262 without a support structure 260, or only one display 251 can be included as part of the HMD 250.

Figure 3A:
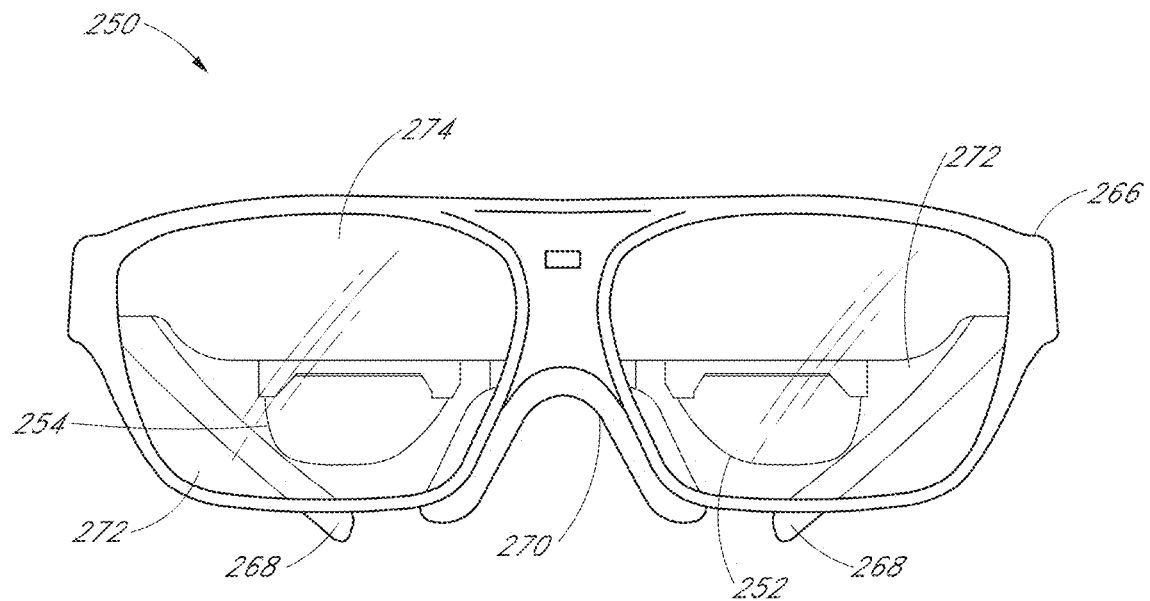
FIGS. 3A and 3B are diagrams illustrating an embodiment of a head mounted display including two stereoscopic displays mounted on a frame.
Figure 3B:
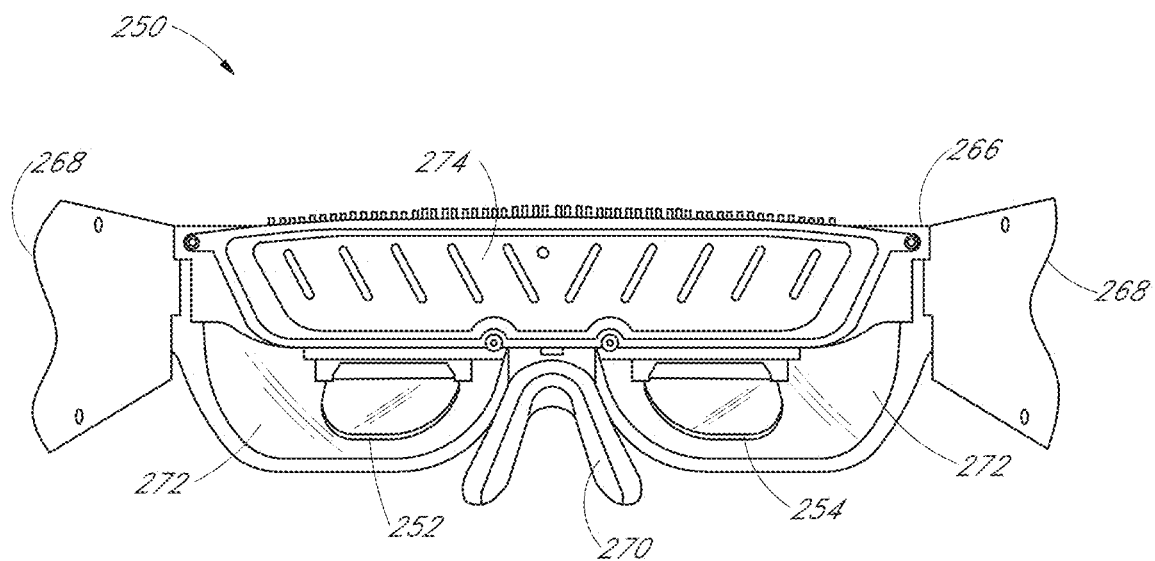

FIGS. 3A and 3B are diagrams illustrating front and back views of an embodiment of an HMD 250. In the illustrated embodiments of FIGS. 3A and 3B, the HMD 250 includes stereoscopic displays 252, 254 mounted on a frame 266, earpieces 268, nose pad 270, an image sensor 271, transparent lenses 272, and an enclosure 274.

The displays 252, 254 can display stereoscopic images for right eye and left eye viewing, as described in greater detail above. In the illustrated embodiment, the displays 252, 254 are opaque and occlude approximately 26° horizontally and approximately 15° vertically of a wearer's field of view. However, as described above, the displays 252, 254 can be sized to occlude different amounts of a wearer's field of view and can be placed in a variety of locations (non-limiting examples: above eye level, below eye level, to the left or right, etc.). However, although the illustrated embodiment of FIGS. 3A and 3B illustrate two displays 252, 254, it will be understood that the HMD 250 can include only a single display providing a left-eye view, right-eye view, or monocular view. In some cases, the use of a single display can reduce weight and cost, and increase battery life of the HMD 250 relative to two displays. Further, it will be understood that the HMD 250 can include more than two displays.

The earpieces 268 and nose pad 270 can support the HMD 250 on the head of a wearer. In some embodiments, the frame 266 can be a frame 266 designed for medical use, such as to receive surgical or dental loupes, or can be any other type of eyeglass frame 266. The space within the frame 266 in the wearer's field of view can be empty, or can include transparent lenses 272 to allow the wearer to observe her surroundings. In some implementations, transparent lenses 272 can provide the advantage of eye protection, such as in surgical and/or dental applications where the wearer can be exposed to airborne biological matter or other hazards.

The enclosure 274 can enclose processing circuitry used to display images on the displays 252, 254. For example, the enclosure 274 can enclose a processor, memory, battery, image sensor, a communication device, one or more emplacement sensors and/or a tracker system, etc. However, it will be understood that the enclosure 274 can enclose fewer or more components as desired. For example, the emplacement sensors and/or a tracker system may be located exterior to the enclosure 274, etc.

The communication device can be used to communicate data to and from other components of the guidance system 101. For example, the communication device can send and/or receive the medical images from the medical imager and the tracking sensor data. The communication device can communicate the data via a wired or wireless communication protocol, such as Bluetooth, Wi-Fi, cellular, Ethernet, USB, etc. In some embodiments, the communication device includes an antenna for wireless communication.

The processor can be implemented using a microprocessor, microcontroller, field programmable gate array, or the like and can process the data received by the communication device or generated at the HMD 250, and perform any one or any combination of the various functions, methods, or routines described herein, similar to the image guidance unit 104 and/or position sensing unit 106, described previously with reference to FIG. 1A. In some embodiments, the guidance system can be communicatively coupled to the HMD 250, either as part of the HMD 250 or as a separate device, such as the image guidance unit 104, etc.

The memory can store non-transitory computer-readable instructions that when executed by the processor cause the processor to perform the various functions, methods, and routines described herein. The battery can be used to provide the HMD 250 with electrical power in order to process the data and display the images on the displays 252, 254. In some embodiments, such as when the HMD 250 receives electrical power from an external source the battery can be omitted.

The image sensor 271 can be used to image the area in front of the HMD 250. In some embodiments, the image sensor 271 can be used as a tracking sensor or tracker system to determine the emplacement of the wearer or HMD 250 relative to the other components of the guidance system 101.

The one or more emplacement sensors or tracker systems can be used to determine the emplacement of the wearer or HMD 250 relative to the other components of the guidance system 101. The emplacement sensor or tracker system can be located within the enclosure 274 or exterior to the enclosure. In some embodiments, the emplacement sensor is located elsewhere on a user, such as on a band around the head or clipped to a jacket of the user, etc. In certain embodiments, the emplacement sensor or tracker system associated with the HMD 250 can use a different coordinate system than the emplacement sensors associated with the medical devices 112, 114. However, it will be understood that in some cases, the emplacement sensors associated with the HMD 250 or user and the emplacement sensors associated with the medical devices 112, 114 can use the same coordinate system.

The HMD 250 can include fewer or more components as desired. For example, in some embodiments, such as when the data from the various emplacement sensors and medical devices is processed outside the HMD 250, the HMD 250 can omit the enclosure 274 and/or some of the components enclosed within the enclosure.

Orbital Mode

Figure 4A:
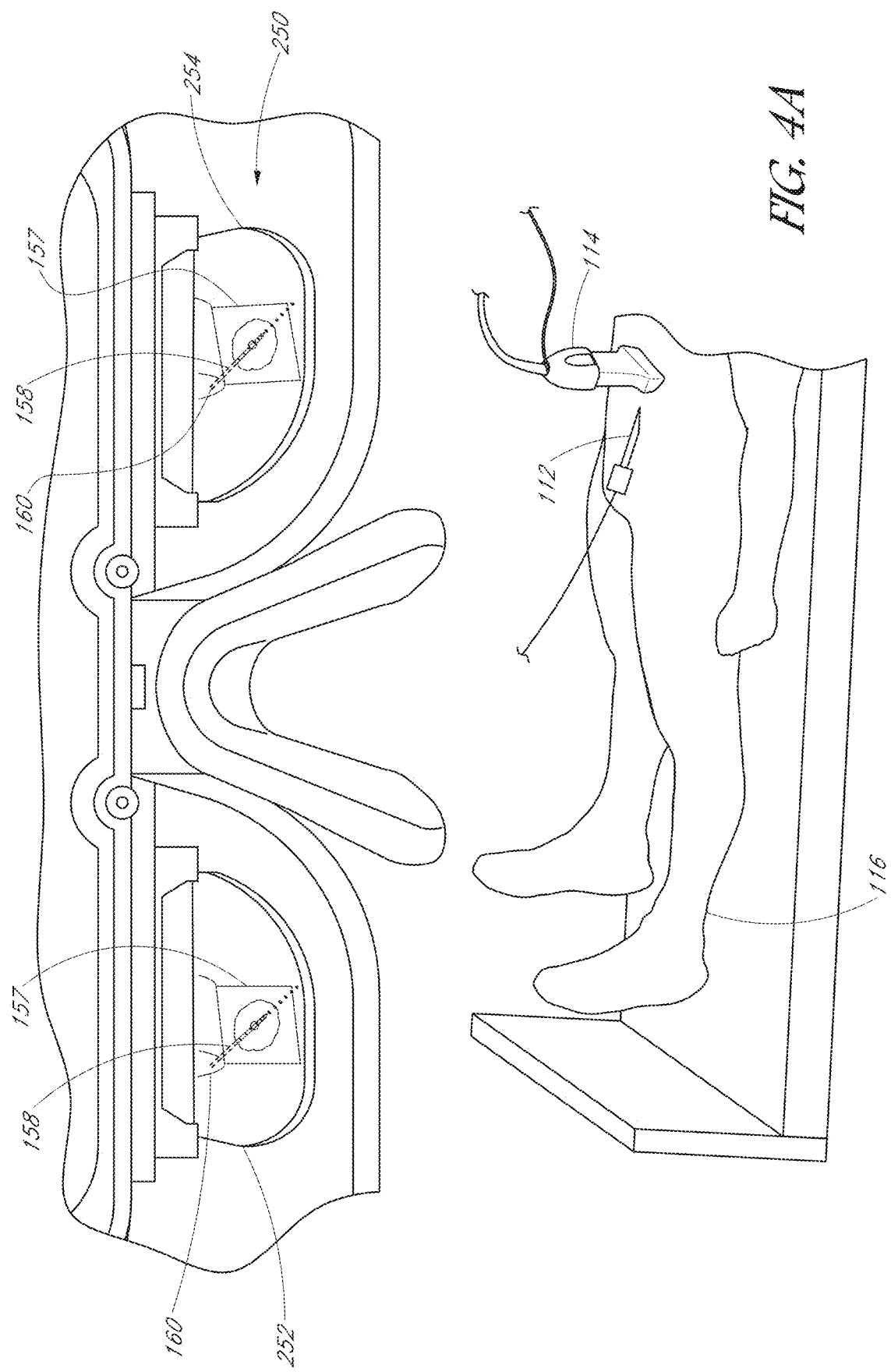
FIG. 4A is a diagram illustrating an embodiment of an orbital view mode.

FIG. 4A is a diagram illustrating an embodiment of an orbital view mode for content displayed on the display 102 and/or displays 252, 254. The orbital view mode can be used to adjust a viewing angle, or perspective view, of the contents of the virtual 3D scene or virtual 3D volume.

Consider an embodiment in which a surgeon is wearing the HMD 250 while performing a surgical procedure on a patient 116 with an ablation needle 112 and an ultrasound probe 114, while being assisted by 3D virtual image content as described above. The surgeon, standing at the patient's side, may desire to view the image slice 157 and a virtual medical device 158 at a different angle, such as to improve the surgeon's awareness of the location of the medical device 112 within the body of the patient. For example, the surgeon may wish to view the virtual image content from a location near the head of the patient 116 (non-limiting example: from a view angle approximately 90 degrees from the current view angle). The orbital view mode can permit the surgeon to change the viewing angle, or perspective view, of the virtual image content by rotating her head, rather than moving relative to the patient 116. In the reference frame of the wearer of an HMD 250, the orbital view mode can cause the displayed virtual object to appear to "orbit" the wearer's head while maintaining its position in the center of the wearer's field of view. In the reference frame of a display 252, 254 of the HMD 250, the virtual object can remain stationary, but can rotate in the direction opposite the rotation of the wearer's head and the HMD 250.

In some embodiments, rotation of the tracking sensor associated with the user about an axis can cause the objects within the virtual 3D scene to rotate about a similar axis in an opposite direction. For example, for the sake of simplicity, consider an embodiment in which the coordinate system for a user is: x-axis is left-right, y-axis is up-down, and z-axis is forward-backward (origin at the center of the user's head) and the coordinate system for a display object is x-axis is left-right, y-axis is up-down, and z-axis is into/out of the display (origin at the center of the object). If a user turns their head to the right (rotates about the user y-axis in a clockwise manner), then the objects within the virtual 3D scene can rotate to the left (rotate about the display object y-axis in a counter-clockwise manner), or the viewing angle can move to the right relative to the origin of the virtual 3D scene. From the perspective of a room coordinate system, the object can orbit around the user's head while maintaining its orientation. In this way, if an image slice is edge-on or approximately edge-on and the user wants to see the right side of the image slice, the user can rotate their head to the left. Similarly, if the user wants to see the left side of an edge-on image slice, the user can turn their head to the right (rotation of head about the user y-axis in a counter-clockwise direction causes the content of the virtual 3D scene to rotate about the display object y-axis in a clockwise manner).

The orbital mode can work with any axis. For example, if the user wants to see to the bottom of an object in the virtual 3D scene she can look up or if the user wants to see to the top of an object in the 3D scene she can look down (rotation of head about x-axis in one direction causes the contents of the virtual 3D scene to rotate about the x-axis in the opposite direction).

With reference to FIG. 4A, the wearer of the HMD 250, the patient 116, and the medical devices 112, 114 can be in the same location as in FIG. 1B. However, the head of the wearer (along with the HMD 250 mounted thereon) has rotated to the left in a counter-clockwise manner such that the wearer's field of view is centered at the lower portion of the patient 116.

Based on the determined orientation change of the HMD 250, the orientation of the contents of the virtual 3D scene, specifically the virtual medical devices 158, 160 and the image slice 157 within the displays 252, 254 have rotated clockwise such that a larger portion of the image slice 157 is visible and the virtual needle 158 which was seen pointing to the wearer's right in FIG. 1B now appears to be pointing towards the wearer in FIG. 4A. Thus, the orbital view mode can enable a wearer to adjust the perspective view of the virtual 3D scene while remaining in the same location and rotating the wearer's head.

In certain embodiments, the orbital mode can be specific to one or more display objects within the 3D scene or to the 3D scene as a whole. For example, based on the rotation of the user, the medical image and/or one or more virtual medical devices can rotate alone or in combination. It will be understood that the orbital mode can also be configured such that the objects within the virtual 3D scene rotate about a different axis and/or in the same direction as axis of rotation and direction of rotation of the tracking sensor.

Furthermore, in some embodiments, the rotation of the display objects can be delayed for a predetermined time period, such as 500 ms. It will be understood that the predetermined time period can be greater than or less than 500 ms. Following the delay, the display objects can move to the new emplacement. In some embodiments, the display objects can lag behind the movement and/or rotate at a rate that is slower than the rotation of the wearer.

Perspective Zoom Mode

Figure 4B:
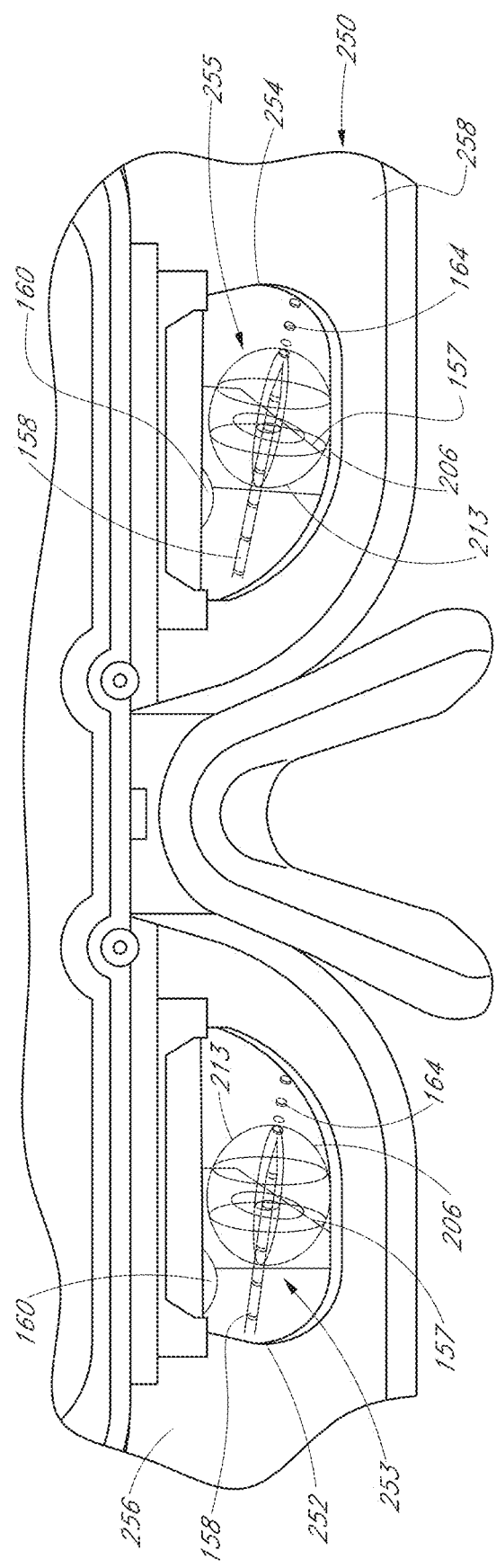
FIG. 4B is a diagram illustrating an embodiment of a perspective zoom mode for displayed content.
Figure 4B:
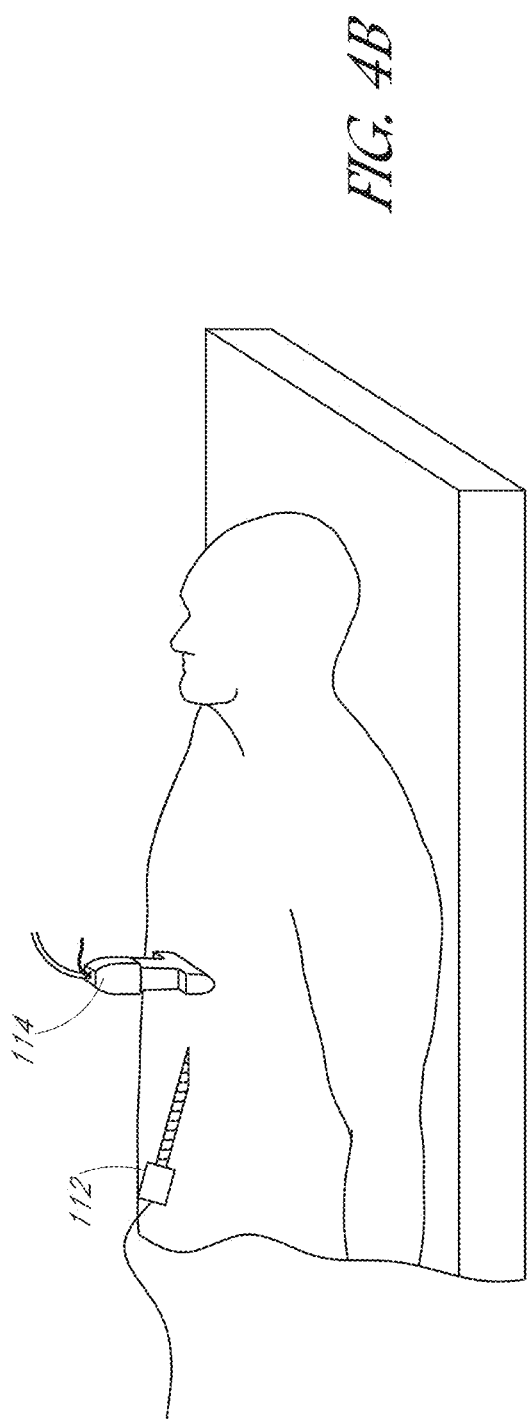

FIG. 4B is a diagram of illustrating an embodiment of a perspective zoom mode. The perspective zoom mode can be implemented independently of or in conjunction with the orbital view mode described with reference to FIG. 4A and/or can be implemented on a HMD 250 and/or the display 102. The perspective zoom mode can further be implemented in combination with a manual zoom function, wherein the magnification or zoom of virtual image content can be selected by a user, such as a wearer of the HMD 250 or viewer of the display 102.

In some embodiments, the zoom, magnification, or similar quality of a displayed image can be determined based at least in part on the orientation of an image slice 157 or a virtual medical device 160 associated with the image slice 157, relative to a point-of-view location.

As a non-limiting example, the image slice 157 can be an ultrasound image slice. A user can position the ultrasound transducer 114 parallel to a point-of-view plane (such that the entire ultrasound image slice is visible on the display similar to a non-perspective view of the ultrasound image slice). In such an orientation, the ultrasound image slice 157 can fill a majority of each display 252, 254 (or display 102). However, when the orientation of the ultrasound image slice 157 within the displays 252, 254 changes (non-limiting examples, the user rotates the medical device 114 towards perpendicular to the point-of-view plane or if the user rotates the ultrasound transducer 114 or rotates her head in an orbital view mode as described above), less of the ultrasound image slice 157 may be visible and the content of the ultrasound image slice 157 can be more difficult to view due to foreshortening.

In such a scenario, the system 101 can increase the size of the displayed image slice 157 based at least in part on the detected change in size of the displayed image slice 157 due to the change in orientation. In some embodiments, the system 101 can zoom in such that the width of the image slice 157 in at least one location within the display fills a substantially constant fraction of the width of each display 252, 254 (or display 102). For example, the system 101 can determine that the pixel width of the ultrasound image slice 157 changed from 500 pixels to 300 pixels due to the change in orientation. As such, the system 101 can increase the overall size of the image slice 157 to take up more space on the displays 252, 254 (or display 102). For example, the system 101 can increase the size of the image slice 157 so that its width at a particular point is 500 pixels (or greater) or at least larger than 300 pixels. When increasing the width of the image slice 157, the system 101 can maintain the aspect ratio of the image slice 157 such that the height of the image slice 157 is increased in relation to the increase of the width of the image slice 157. Accordingly, the system 101 can increase the size of the image slice 157 while maintaining its shape (and perspective).

Similarly, the system 101 can use a change in height of the image slice 157 to adjust the size of the image slice 157. For example, the system 101 can enlarge the image slice 157 such that the height of the image slice 157 in at least one location maintains a relatively constant height or relatively constant fraction of the height of the displays 252, 254. Any combination of the height or width of the image slice 157 can be used as desired.

In various embodiments, the aspect ratio of the image slice 157 can cause the height of the image to exceed the vertical or horizontal dimension of the displays 252, 254 when enlarged. Where the perspective zoom setting results in a vertical dimension of image slice 157 exceeding the height of displays 252, 254, the image slice 157 can remain vertically centered within the displays 252, 254, or the displays 252, 254 can remain centered on a selected location within the image slice 157, such as a location of a tumor or other targeted structure. In certain embodiments, the system 101 can increase the size of the image slice 157 based on the size of the displays 252, 254. For example, the system 101 can increase the size of the image slice 157 while maintaining a view of the entire image slice 157 within the displays 252, 254. As a non-limiting example, the system 101 can enlarge the image slice 157 such that at least two points of the image slice 157 are proximal to the edge of the display area, such as within a few pixels of the edge of the display area.

Furthermore, the system 101 can use the image slice 157 in combination with one or more additional display objects to determine the amount of enlargement. For example, the system 101 can use a size of the image slice in combination with the virtual medical device 160 to determine the amount by which they are to be enlarged. In this way, the system 101 can enlarge the image slice 157 while maintaining the display of other display objects. Any one or any combination of the aforementioned embodiments can be used as desired.

With reference to FIGS. 1B and 4B, the ultrasound 114 of FIG. 4B has been rotated counter-clockwise relative to the ultrasound 114 of FIG. 1B. As such, the medical image 157 has changed to be closer to edge-on in FIG. 4B. As the medical image 157 is moves closer to edge-on and its contents become less visible, the system 101 enlarged the size of the display objects on the displays 252, 254. As part of the enlargement, or zoom-in, less of the virtual medical devices 158, 160 are visible. However, by enlarging the display objects, the user is able to have a better view of the contents of the medical image 157, despite the medical image 157 being closer to edge-on.

Multiple Users

Figure 4C:
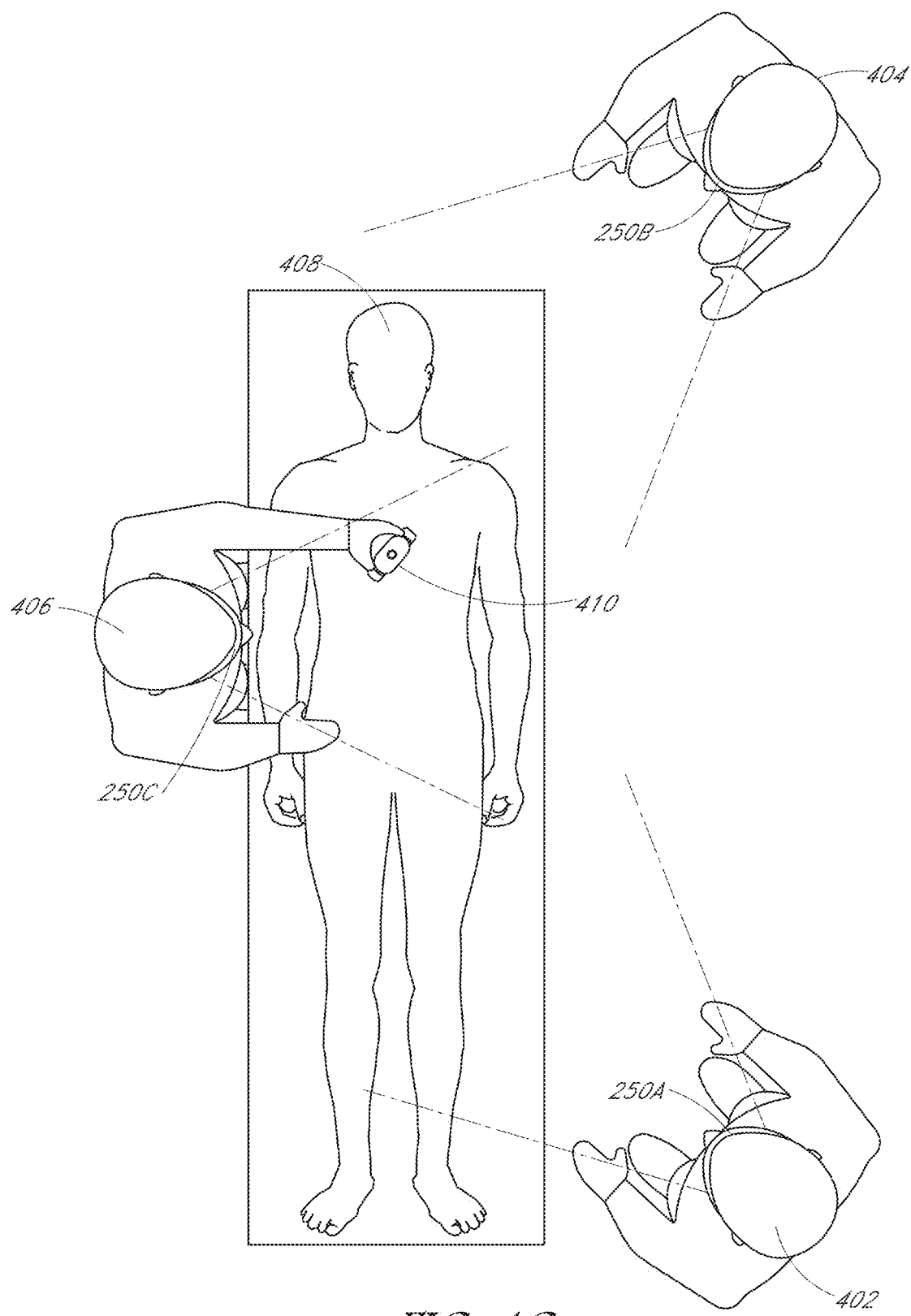
FIG. 4C is a diagram illustrating an embodiment showing multiple users using head mounted displays.

FIG. 4C is a diagram illustrating an embodiment in which multiple users 402, 404, 406 in an environment 400 can view the environment 400, including the patient 408, and view a virtual scene using HMDs 250A, 250B, 250C, respectively (generically referred to as HMDs 250). In medical applications, there are often multiple doctors around a patient, all of which would benefit from seeing a view of the virtual 3D scene, from their own point of view. One way to enable this benefit is for each doctor to wear their own head mounted display, each of which can be tracked by the guidance system as described in greater detail above. Accordingly, each head mounted display can show the 3D scene from its own tracked location.

In some embodiments, each of the users 402, 404, 406 can have an unobstructed view of the patient 408 and view the 3D scene on the HMDs 250 from their own point of view. In certain embodiments, the view of the patient 408 can be obstructed depending on the location of the users 402, 404, 406 with respect to the patient. As a non-limiting example, if the user 402 sees the front side of a 3D rendering of the ultrasound probe 410 and of a rendering of the ultrasound image corresponding to the ultrasound probe 410 on his HMD 250A, the user 406 can view the back side of the 3D rendering of the ultrasound probe 410 and of the rendering of the ultrasound image corresponding to the ultrasound probe 410 on his HMD 250C. Similarly, the user 404 can have an approximate edge-on view of the ultrasound image corresponding to the ultrasound probe 410 on his HMD 250B. Each user having their own view of the 3D scene based on their emplacement in the environment 400 enables interaction between the users in a shared physical and virtual space.

In some scenarios, the patient 408 can also use a HMD 250. For example, in a physical therapy environment, the physical therapist and patient could both wear their own HMD 250, and as the physical therapist uses an ultrasound probe to show the patient a muscle injury, the physical therapist and patient could see the injury from their own point of view.

It will be understood that different users cans also see a different view using different display technologies. For example, one user can use a TV with a view configured for her location in the room, whereas a second user could wear a tracked HMD 250 that would show her the 3D scene from her own point of view.

Flow Diagrams

Figure 5:
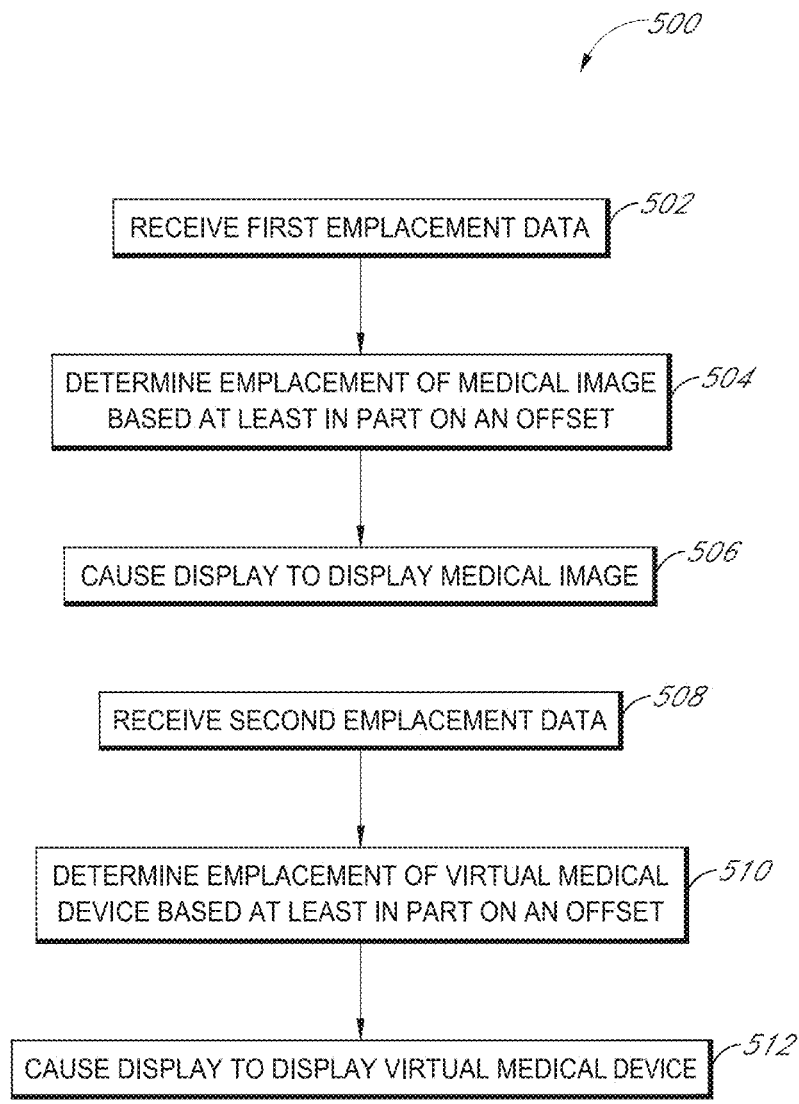
FIG. 5 is a flow diagram illustrative of an embodiment of a routine implemented by the system to display medical image content.

FIG. 5 is a flow diagram illustrative of an embodiment of a routine 500 implemented by the system 101 to display medical image content. One skilled in the relevant art will appreciate that the elements outlined for routine 500 can be implemented by one or more computing devices/components that are associated with the system 101, such as the position sensing unit 106, the image guidance unit 104, surgical system 108, the HMD 250, and/or the imager 110. Accordingly, routine 500 has been logically associated as being generally performed by the system 101. However, the following illustrative embodiment should not be construed as limiting. Furthermore, it will be understood that the various blocks described herein with reference to FIG. 5 can be implemented in a variety of orders. For example, the system 101 can implement some blocks concurrently or change the order as desired.

At block 502, the system 101 receives first emplacement data associated with a first emplacement sensor and/or a medical device. The first emplacement data can be generated by the first emplacement sensor and/or by a position sensing unit. In some embodiments, the first emplacement sensor can be associated with the medical device. For example, the first emplacement sensor can be associated with and/or attached to an ultrasound transducer, needle, etc., as described above.

At block 504, the system 101 determines an emplacement of a medical image based at least in part on received first emplacement data and an offset. The medical image can be an intra-operative and/or real-time medical image, such as a live ultrasound or intra-operative CT scan, or can be a pre-operative image, such as a pre-operative CT or MRI scan image. A real-time medical image (or real-time medical imaging stream) can refer to a medical image (or real-time medical imaging stream) received in real-time. The medical image received in real-time can correspond to a live image, such as a live ultrasound image generated by an ultrasound or other image, such as a pre-operative or intra-operative CT image or MRI image that is communicated in real-time.

In some embodiments, the system 101 can use the first emplacement data and one or more characteristics of the first emplacement sensor or associated medical device (or a corresponding virtual medical device) to determine the emplacement of the medical image. For example, the characteristics may indicate an emplacement of the medical image relative to the first emplacement sensor or associated medical device (or virtual medical imaging device).

Using this information, the system 101 can determine the emplacement of the medical image relative to the first emplacement sensor and/or associated medical device (or virtual medical imaging device). For example, the system 101 can use a known relationship between the first emplacement data and the emplacement of the medical image (non-limiting example: the medical image begins 2 cm. away from the of the first emplacement data location in a particular direction and ends 5 cm. away) and/or use a known relationship between the emplacement of the first emplacement sensor and/or associated medical device (or virtual medical imaging device) and the emplacement of the medical image (non-limiting examples: the medical image begins 4 cm. from the tip of the medical device (or virtual medical imaging device) and ends at the tip of the medical device (or virtual medical imaging device), or the medical image extends 2 cm. in either direction from the ends of the first emplacement sensor).

In addition, in certain embodiments, the system 101 can determine the emplacement of the medical image in one or more coordinate systems and/or by mapping the first emplacement data, from one coordinate system to a second coordinate system. For example, the first emplacement data may be received with respect to a first coordinate system, such as a position sensing coordinate system, and then mapped to a second coordinate system, such as a 3D scene coordinate system and/or a screen coordinate system. The emplacement of the medical image can be determined with respect to one or more of the coordinate systems. For example, the emplacement of the medical image can be determined after the first emplacement data has been mapped to the second coordinate system, such as the 3D scene coordinate system and/or the screen coordinate system, or the emplacement of the medical image can be determined for the first coordinate system, such as the position sensing coordinate system, and then mapped to the 3D scene coordinate system and/or the screen coordinate system.

In certain embodiments, the system 101 can also use an offset to determine the emplacement of the medical image for viewing. For example, the system 101 can determine an initial emplacement of the medical image in the 3D scene coordinate system and/or the screen coordinate system, and then apply an offset to the initial emplacement and/or the system 101 can determine an initial emplacement of the medical image in the position sensing coordinate system and apply an offset to the initial emplacement prior to mapping the emplacement of the medical image in the position sensing coordinate system to the 3D scene coordinate system and/or the screen coordinate system.

The offset can be made in one, or a combination of, coordinate systems, and/or with respect to one, or a combination of, axes. In certain embodiments, the offset can be made along a y-axis (up/down) of the position sensing coordinate system, the 3D scene coordinate system and/or the screen coordinate system. For example, the system 101 can adjust the y-coordinate (up/down coordinate) of the determined emplacement of the medical image (or the first emplacement sensor) in the position sensing coordinate system by the offset amount. When mapped to the 3D scene coordinate system and/or the screen coordinate system, the system 101 can use the adjusted emplacement. As yet another example, the system 101 can adjust the y-coordinate (up/down coordinate) of the determined emplacement of the medical image (or the first emplacement sensor) in the 3D scene coordinate system and/or the screen coordinate system by the offset amount. Any combination of the above-referenced examples can be used as desired. Furthermore, it will be understood that the offset can be made in any one or any combinations of the coordinate systems and with reference to any one or any combination of the axes. For example, the adjustment can be made along any one or any combination of the x-axis, y-axis, or z-axis.

Furthermore, the offset can be a predetermined offset and/or a dynamic offset. In some embodiments, a predetermined offset can be used. For example, the system 101 can use a static offset based on an average height of males and/or females or average distance between elbows and hands, the height of the user, a distance between the user's elbow and eyes, expected location of a user with respect to the imaged volume, etc. In certain embodiments, the system 101 can use a dynamic offset, such as a determined emplacement of the HMD 250 relative to one or more emplacement sensors, position sensing region, and/or position sensing unit coordinate system. For example, the system 101 can determine the emplacement of the HMD 250 relative to a medical device or imaged area and adjust the offset such that the medical image is always in view on the displays of the HMD 250. With continued reference to the example, if the wearer crouches down or turns to the side, the system 101 can determine the change in relative emplacement between the HMD 250 and the medical device or imaged area and adjust the offset such that the medical image remains in view in substantially the same emplacement.

In addition, it will be understood that the offset described herein with reference to the medical image can be applied to any one or any combination of the objects to be displayed and/or to all contents of the virtual 3D scene. In some embodiments, the offset can be applied to some objects to be displayed but not others.

At block 506, the system 101 can cause a display to display a view of a virtual 3D scene including a perspective rendering of the medical image based at least in part on the determined emplacement of the medical image. As described above, the perspective view or rendering the medical image can be determined and displayed based at least in part on a point-of-view location. The point-of-view location can be a fixed point-of-view location or a dynamic point-of-view location. For example, the point-of-view location can be with respect to a set location in front of the display and/or can be based on a tracked location of the display, the HMD, or the user. In some embodiments, the point-of-view location is determined based at least in part on the relative emplacement of the HMD or user with respect to the position sensing region or imaged volume, or the emplacement of the HMD within a position sensing coordinate system. In embodiments, in which the point-of-view location is based on a tracked location, the system 101 can enable the user to view different perspective views of the virtual 3D scene based on the changing emplacement of the tracked object (HMD, user) relative to the medical devices 112, 114 or the position sensing region.

It will be understood that the various blocks described herein can be implemented in a variety of orders, and that the system 101 can implement one or more of the blocks concurrently and/or change the order, as desired. For example, the system 101 can concurrently receive the emplacement data from different sources, concurrently receive the medical image, or receive the data in any order. Similarly, the system 101 can concurrently determine the emplacement of the medical image and/or one or more virtual medical devices, etc.

Furthermore, it will be understood that fewer, more, or different blocks can be used as part of the routine 500. For example, the routine 500 can include blocks for receiving emplacement data associated with additional emplacement sensors or medical devices, determining emplacements of one or more medical devices, corresponding virtual medical devices, other display objects, displays, and/or users. In some embodiments, the routine 500 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 101 can determine and display a variety of image guidance cues, such as trajectory indicators, affected region indicators, as described above.

In certain embodiments, the system 101 can determine multiple emplacements for the medical image. For example, the system 101 can determine the emplacement for the medical image for a right-eye view and a left-eye view of a stereoscopic display, such for the HMD 250. In this way, each display for the HMD 250 can display the medical image from a slightly different perspective corresponding to a right-eye view and a left-eye view, etc.

In some embodiments, the routine 500 can further include any one or any combination of blocks 508, 510, and/or 512. At block 508, the system 101 can receive second emplacement data associated with a second emplacement sensor and/or a second medical device. The second emplacement data can be generated by the second emplacement sensor and/or by the position sensing unit. In some embodiments, the second emplacement sensor can be associated with the second medical device. For example, the second emplacement sensor can be associated with and/or attached to an ultrasound transducer, needle, etc.

At block 510, the system 101 can determine an emplacement of a virtual medical device based at least in part on the received second emplacement data and an offset. The system 101 can determine the emplacement for the virtual medical device similar to the manner in which the system 101 determines the emplacement of the medical image as described above with reference to block 504. In some embodiments, the offset for the virtual medical device can be the same as the offset for the medical image. In certain embodiments, the offset for the virtual medical device can be different from the offset for the medical image.

At block 512, the system 101 can include the medical image in the virtual 3D scene and cause the stereoscopic display to concurrently display a perspective rendering of the virtual medical device based at least in part on the determined emplacement of the virtual medical device, similar to the display of the medical described above with reference to block 506. In some embodiments, the display of the virtual medical device can be based at least in part on dimensions of a corresponding real medical device (non-limiting examples: size, shape, or other appearance).

Figure 6:
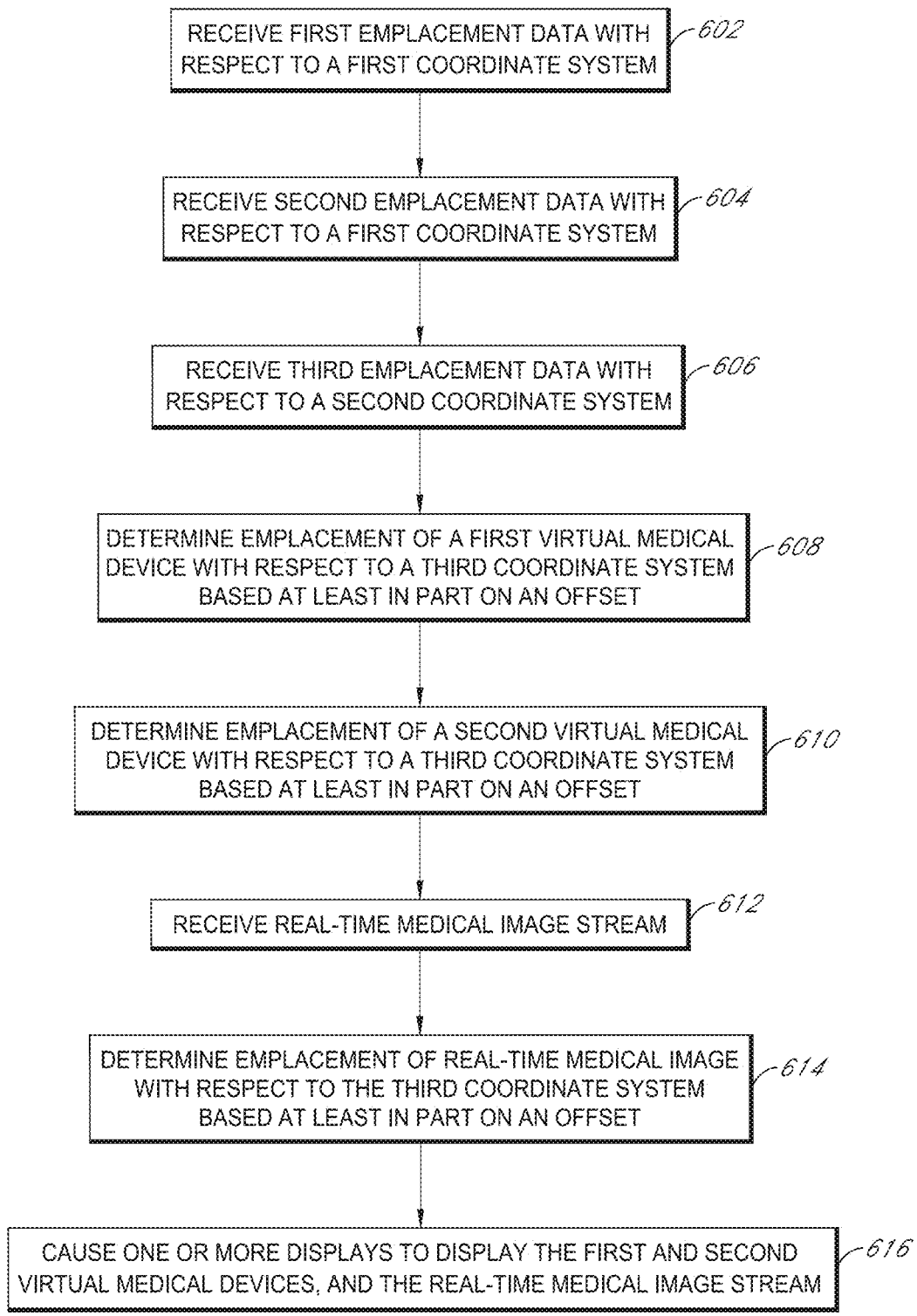
FIG. 6 is a flow diagram illustrative of an embodiment of a routine implemented by the system to display medical image content.

FIG. 6 is a flow diagram illustrative of an embodiment of a routine 600 implemented by the system 101 to display medical image content. One skilled in the relevant art will appreciate that the elements outlined for routine 600 can be implemented by one or more computing devices/components that are associated with the system 101, such as the position sensing unit 106, the image guidance unit 104, surgical system 108, the HMD 250, and/or the imager 110. Accordingly, routine 600 has been logically associated as being generally performed by the system 101. However, the following illustrative embodiment should not be construed as limiting. Furthermore, it will be understood that the various blocks described herein with reference to FIG. 6 can be implemented in a variety of orders. For example, the system 101 can implement some blocks concurrently or change the order, as desired.

At block 602, the system 101 receives emplacement data associated with a first emplacement sensor or first medical device with respect to a first coordinate system. At block 604, the system 101 receives emplacement data associated with a second emplacement sensor or second medical device with respect to the first coordinate system. The first emplacement data and second emplacement data can be generated by the first emplacement sensor and second emplacement sensor, respectively, and or by a position sensing unit tracking the first emplacement sensor and the second emplacement sensor. In some embodiments, the first emplacement sensor is associated with the first medical device and the second emplacement sensor is associated with the second medical device. For example the emplacement sensors can be attached to the respective medical device and/or embedded within the respective medical device, etc. The first coordinate system can correspond to a coordinate system associated with the position sensing unit that is tracking the first and second emplacement sensors.

At block 606, the system 101 can receive third emplacement data associated with a third emplacement sensor or third object with respect to a second coordinate system. The third emplacement sensor can be associated with a user. For example, the third emplacement sensor can be an emplacement sensor associated with an HMD or other device attached to the user. The third emplacement data can be generated by the third emplacement sensor and/or by a position sensing unit tracking the third emplacement sensor. In some embodiments, the second coordinate system can be different from the first coordinate system, such as when one position sensing unit is tracking the first and second emplacement sensors and a different position sensing unit is tracking the third emplacement sensor. For example, in some embodiments, a magnetic position sensing unit can track the first and second emplacement sensors and an optical position sensing unit can track the third emplacement sensor. In certain embodiments, such as when the same position sensing unit is tracking the first, second, and third emplacement sensors, the first and second coordinate system can be the same coordinate system. As described previously, in embodiments in which the first and second coordinate systems are different, the system 101 can map coordinates from one coordinate system to the other coordinate system and vice versa.

At block 608, the system 101 can determine an emplacement of a first virtual medical device with respect to a third coordinate system based at least in part on the received first emplacement data, an offset, and the third emplacement data. In some embodiments, the third coordinate system can be a coordinate system associated with a 3D stereoscopic display.

In some embodiments, the system 101 can use the first emplacement data and/or characteristics of the first emplacement sensor relative to a medical device to determine the emplacement of the virtual medical device. For example, the characteristics may indicate an emplacement of the medical device relative to the first emplacement sensor. Using this information, the system 101 can determine the emplacement of the virtual medical device corresponding to the medical relative to the first emplacement sensor.

Furthermore, in certain embodiments, the system 101 can determine the emplacement of the virtual medical device in the third coordinate system by mapping the first emplacement data from the first coordinate system to the third coordinate system. For example, the first emplacement data can be received with respect to a position sensing coordinate system and then mapped to a 3D scene coordinate system and/or a screen coordinate system.

Using the mapping of the first emplacement data from the first coordinate system to the third coordinate system, the system 101 can determine the emplacement of the virtual medical device. In some embodiments, the system 101 can map the first emplacement data to the third coordinate system and then determine the emplacement of the virtual medical device and/or determine the emplacement of a medical device corresponding to the virtual medical device in the first coordinate system and then map the emplacement of the medical device to the third coordinate system. For example, the system 101 can determine the emplacement of a needle in a position sensing coordinate system (the first coordinate system for this example) based at least in part on the first emplacement data and then map the determined emplacement of the needle to a 3D scene coordinate system and/or a screen coordinate system (the third coordinate system for this example). The emplacement of the needle mapped to the 3D scene coordinate system and/or the screen coordinate system can correspond to the emplacement of the virtual needle in the 3D scene coordinate system and/or screen coordinate system. With continued reference to the example, the system 101 can map the first emplacement data from the position sensing coordinate system to the 3D scene coordinate system and/or screen coordinate system and then based on dimensions of the needle, determine the emplacement of the virtual needle in the 3D scene coordinate system and/or screen coordinate system.

Furthermore, the system 101 can use the third emplacement data to determine the emplacement of the virtual medical device in the third coordinate system. In some embodiments, the third emplacement data can be used to determine the point-of-view location for the user, or the perspective from which the virtual medical device (or contents of the virtual 3D scene) is to be displayed to the user. In this way, as the user moves from side to side, the view of the virtual medical device (or contents of the virtual 3D scene) can change, similar to the way in which the view of an object changes as a person walks around the object.

At block 610, the system 101 can determine an emplacement of a second virtual medical device with respect to the third coordinate system based at least in part on the received second emplacement data, the offset, and the third emplacement data. Similar to the determination of the first virtual medical device as described in greater detail above with reference to block 608, the system 101 can determine the emplacement for the second virtual medical device with respect to the third coordinate system.

At block 612, the system 101 can receive a real-time medical image stream associated with the second virtual medical device. For example, the medical image stream can be a stream of ultrasound images obtained from an ultrasound transducer connected to the second emplacement sensor and/or can be a stream of CT images registered with the patient and received based at least in part on the emplacement of a medical device relative to the patient.

At block 614, the system 101 can determine an emplacement of the real-time medical image stream with respect to the third coordinate system based at least in part on the received second emplacement data, the offset, and the third emplacement data. As described in greater detail above with reference to block 504 of FIG. 5, the system 101 can determine the emplacement of the real-time medical image stream by mapping the first emplacement data to the third coordinate system. In certain embodiments, the system 101 can use the one or more characteristics of the first emplacement sensor or associated medical device (or a corresponding virtual medical device) to determine the emplacement of the medical image. In addition, as described in greater detail above with reference to block 608, the system 101 can use the third emplacement data to determine a point-of-view location for the user, or a perspective from which the real-time medical image stream (or contents of the virtual 3D scene) is to be displayed to the user.

At block 616, the system 101 can cause a display to display a rendered view of a virtual 3D scene including the first virtual medical device, the second virtual medical device, and the real-time medical image stream, as described in greater detail above. In certain embodiments, the contents of the virtual 3D scene can be displayed concurrently. In some embodiments, the system 101 generates two views of the virtual 3D scene for different perspectives for display on the display. One view can be a right-eye view and the other can be a left-eye view.

In some embodiments, the system can display the virtual 3D scene using the third coordinate system. For example, the third coordinate system can refer to a display coordinate system. In certain embodiments, the system can map the content of the virtual 3D scene from a third coordinate system to fourth and fifth coordinate systems before displaying. For example, the third coordinate system can refer a 3D scene coordinate system and the fourth and fifth coordinate systems can refer to left-eye, right-eye stereoscopic display coordinate systems.

It will be understood that the various blocks described herein can be implemented in a variety of orders. The system 101 can implement one or more of the blocks concurrently and/or change the order, as desired. For example, the system 101 can concurrently receive the first, second, and/or third emplacement data, concurrently receive additional emplacement data, concurrently receive the medical image stream, or receive the data in any order. Similarly, the system 101 can concurrently determine the emplacement of the virtual medical devices and/or medical image stream as desired.

Furthermore, it will be understood that fewer, more, or different blocks can be used as part of the routine 600. For example, the routine 600 can include blocks for receiving emplacement data associated with additional emplacement sensors, blocks for determining emplacements of virtual objects associated with the additional emplacement sensors in any of various coordinate systems, and blocks for causing additional virtual objects to be displayed. Furthermore, the system 101 can determine the emplacement for, and cause the display to display, a variety of image guidance cues, such as trajectory indicators, affected region indicators, as described above.

In some embodiments, the system 101 can determine the emplacement of the various virtual medical devices, and medical image stream in additional coordinate systems. For example, the system 101 can determine the emplacement of display objects for a stereoscopic view, including a left-eye view and a right-eye view, and cause multiple one or more displays to display the stereoscopic views.

Although described herein as determining emplacement of medical devices and virtual medical device, and displaying virtual 3D scenes including virtual medical devices and other image guidance cues for medical device guidance, it will be understood that the disclosure herein is not limited to medical device guidance, but can be used in a variety of applications. For example, the HMD with displays that include an opaque portion can be used in other settings or environments where it is desirable to see the environment around the opaque displays. Similarly, displaying a virtual 3D scene using an offset can be used in applications in which a user desires to see an object in real life while concurrently viewing a virtual rendering of the object or cues relevant to the object.

Example Embodiments

Various example embodiments of the disclosure can be described in view of the following clauses:

Clause 1. A method of presenting virtual content to a user of a head mounted display, the method comprising:
  receiving emplacement data associated with a first emplacement sensor with respect to a first coordinate system;
  receiving emplacement data associated with a second emplacement sensor with respect to the first coordinate system;
  receiving emplacement data associated with a third emplacement sensor with respect to a second coordinate system, the third emplacement sensor associated with a head mounted display;
  determining a first emplacement of a first virtual medical device with respect to a third coordinate system based at least in part on the received emplacement data associated with the first emplacement sensor, a predetermined offset, and the received emplacement data associated with the third emplacement sensor;
  determining a first emplacement of a second virtual medical device with respect to the third coordinate system based at least in part on the received emplacement data associated with the second emplacement sensor, the predetermined offset, and the received emplacement data associated with the third emplacement sensor;
  receiving a real-time medical imaging stream associated with the second virtual medical device;
  determining a first emplacement of the real-time medical imaging stream with respect to the third coordinate system based at least in part on the received emplacement data associated with the second emplacement sensor, the predetermined offset, and the received emplacement data associated with the third emplacement sensor;

determining a second emplacement of the first virtual medical device with respect to a fourth coordinate system based at least in part on the received emplacement data associated with the first emplacement sensor, the predetermined offset, and the received emplacement data associated with the third emplacement sensor;

determining a second emplacement of the second virtual medical device with respect to the fourth coordinate system based at least in part on the received emplacement data associated with the second emplacement sensor, the predetermined offset, and the received emplacement data associated with the third emplacement sensor;

determining a second emplacement of the real-time medical imaging stream with respect to the fourth coordinate system based at least in part on the received emplacement data associated with the second emplacement sensor, the predetermined offset, and the received emplacement data associated with the third emplacement sensor;

causing a first opaque stereoscopic display of the head mounted display to display a first 3D rendered view of a virtual 3D volume including:
  a 3D rendering of the first virtual medical device based at least in part on the determined first emplacement of the first virtual medical device,
  a 3D rendering of the second virtual medical device based at least in part on the determined first emplacement of the second virtual medical device, and
  a 3D rendering of the real-time medical imaging stream based at least in part on the determined first emplacement of the real-time medical imaging stream; and causing a second opaque stereoscopic display of the head mounted display to display a second 3D rendered view of the virtual 3D volume including:
  a 3D rendering of the first virtual medical device based at least in part on the determined second emplacement of the first virtual medical device,
  a 3D rendering of the second virtual medical device based at least in part on the determined second emplacement of the second virtual medical device, and
  a 3D rendering of the real-time medical imaging stream based at least in part on the determined second emplacement of the real-time medical imaging stream, wherein the first 3D rendered view and the second 3D rendered view change in relation to a change in the emplacement data associated with the third emplacement sensor.

Clause 2. The method of Clause 1, wherein the first emplacement sensor is associated with a first real medical device and the second emplacement sensor is associated with a second real medical device.

Clause 3. The method of Clause 2, wherein the predetermined offset is configured to allow a wearer of the head mounted display to simultaneously view at least a portion of the first virtual medical device, and at least a portion of the real-time medical imaging stream on the first and second opaque stereoscopic displays, and at least a portion of a first medical device corresponding to the first virtual medical device and the second real medical device corresponding to the second virtual medical device at a location below the first and second opaque stereoscopic displays.

Clause 4. The method of Clause 1, wherein the real-time medical imaging stream comprises at least one ultrasound image.

Clause 5. The method of Clause 1, wherein the first opaque stereoscopic display is at least partially located within, and comprises only a subset of a field of view of a left eye of a wearer of the head mounted display, and wherein the second opaque stereoscopic display is at least partially located within, and comprises only a subset of, the field of view of a right eye of a wearer of the head mounted display.

Clause 6. A method of presenting virtual content to a user, the method comprising:
  receiving first emplacement data associated with a first emplacement sensor with respect to a first coordinate system;
  receiving second emplacement data associated with a second emplacement sensor with respect to the first coordinate system;
  receiving third emplacement data associated with a third emplacement sensor with respect to a second coordinate system, the third emplacement sensor associated with a user;
  determining an emplacement of a first virtual medical device with respect to a third coordinate system based at least in part on the received first emplacement data, a predetermined offset, and the third emplacement data;
  determining an emplacement of a second virtual medical device with respect to the third coordinate system based at least in part on the second emplacement data, the predetermined offset, and the third emplacement data;
  receiving a medical imaging stream associated with the second virtual medical device;
  determining an emplacement of the medical imaging stream with respect to the third coordinate system based at least in part on the second emplacement data, the predetermined offset, and the third emplacement data; and
  causing a display to display a 3D rendered view of a scene including:
    a 3D rendering of the first virtual medical device based at least in part on the determined emplacement of the first virtual medical device,
    a 3D rendering of the second virtual medical device based at least in part on the determined emplacement of the second virtual medical device, and
    a 3D rendering of the medical imaging stream based at least in part on the determined emplacement of the medical imaging stream,
  wherein the 3D rendered view changes in relation to a change in the determined emplacement of the third emplacement sensor.

Clause 7. The method of Clause 6, wherein the first emplacement sensor is associated with a first real medical device and the second emplacement sensor is associated with a second real medical device.

Clause 8. The method of Clause 7, wherein the predetermined offset is configured to allow a viewer of the display to simultaneously view at least a portion of the first virtual medical device and at least a portion of the medical imaging stream on the display, and at least a portion a medical device corresponding to the first virtual medical device above and/or below the display.

Clause 9. The method of Clause 6, wherein the medical imaging stream comprises at least one ultrasound image.

Clause 10. A method of presenting virtual content to a user, the method comprising:

receiving first emplacement data associated with a first emplacement sensor;

determining an emplacement of a medical image based at least in part on the first emplacement data associated with the first emplacement sensor and an offset; and causing a display to display a view of a 3D scene including a perspective rendering of the medical image based at least in part on the determined emplacement of the medical image, wherein the perspective rendering of the medical image varies in relation to a change in the first emplacement data.

Clause 11. The method of Clause 10, further comprising:

determining an emplacement of a virtual medical device based at least in part on the first emplacement data and the offset; and causing the display to display a perspective rendering of the virtual medical device.

Clause 12. The method of Clause 10, further comprising:

receiving second emplacement data associated with a second emplacement sensor;

determining an emplacement of a virtual medical device based at least in part on the second emplacement data and the offset; and causing the display to display a perspective rendering of the virtual medical device.

Clause 13. The method of Clause 12, wherein the second emplacement sensor is associated with a real medical device.

Clause 14. The method of Clause 13, further comprising causing the display to display the perspective rendering of the medical image and the perspective rendering of the virtual medical device using the offset such that a viewer of the display simultaneously views the perspective rendering of the medical image and the perspective rendering of the virtual medical device on the display, and at least a portion of the real medical device above and/or below the display.

Clause 15. The method of Clause 10, further comprising receiving second emplacement data associated with a second emplacement sensor associated with a user and/or a head mounted display, wherein the perspective rendering of the medical image varies in relation to a change in the second emplacement data.

Clause 16. The method of Clause 15, wherein the display comprises an opaque stereoscopic display of the head mounted display.

Clause 17. A guidance system, comprising one or more processors, the guidance system configured to:

receive first emplacement data associated with a first emplacement sensor;

determine an emplacement of a medical image based at least in part on the received first emplacement data an offset; and cause a display to display a perspective rendering of the medical image based at least in part on the determined emplacement of the medical image, wherein the perspective rendering of the medical image varies in relation to a change in the received first emplacement data.

Clause 18. The guidance system of Clause 17, wherein the guidance system is further configured to:

determine an emplacement of a virtual medical device based at least in part on the first emplacement data and the offset; and cause the display to display a perspective rendering of the virtual medical device.

Clause 19. The guidance system of Clause 17, wherein the guidance system is further configured to:

receive second emplacement data associated with a second emplacement sensor;

determine an emplacement of a virtual medical device based at least in part on the second emplacement data and the offset; and cause the display to display a perspective rendering of the virtual medical device.

Clause 20. The guidance system of Clause 19, wherein the second emplacement sensor is associated with a real medical device.

Clause 21. The guidance system of Clause 20, wherein the guidance system is configured to cause the display to display the perspective rendering of the medical image and the perspective rendering of the virtual medical device using the offset such that a viewer of the display simultaneously views the perspective rendering of the medical image and the perspective rendering of the virtual medical device on the display, and at least a portion of the real medical device above and/or below the display.

Clause 22. The guidance system of Clause 17, wherein the guidance system is further configured to receive second emplacement data associated with a second emplacement sensor associated with a user, wherein the perspective rendering of the medical image varies in relation to a change in the second emplacement data.

Clause 23. The guidance system of Clause 17, wherein the display comprises an opaque, stereoscopic display of a head mounted display.

Clause 24. A guidance system in communication with a head mounted display and comprising one or more processors, the guidance system configured to:

receive emplacement data associated with a first emplacement sensor with respect to a first coordinate system;

receive emplacement data associated with a second emplacement sensor with respect to the first coordinate system;

receive emplacement data associated with a third emplacement sensor with respect to a second coordinate system, the third emplacement sensor associated with a head mounted display;

determine a first emplacement of a first virtual medical device with respect to a third coordinate system based at least in part on the received emplacement data associated with the first emplacement sensor, a predetermined offset, and the received emplacement data associated with the third emplacement sensor;

determine a first emplacement of a second virtual medical device with respect to the third coordinate system based at least in part on the received emplacement data associated with the second emplacement sensor, the predetermined offset, and the received emplacement data associated with the third emplacement sensor;

receive a real-time medical imaging stream associated with the second virtual medical device;

determine a first emplacement of the real-time medical imaging stream with respect to the third coordinate system based at least in part on the received emplacement data associated with the second emplacement sensor, the predetermined offset, and the received emplacement data associated with the third emplacement sensor;

determine a second emplacement of the first virtual medical device with respect to a fourth coordinate system based at least in part on the received emplacement data associated with the first emplacement sensor, the predetermined offset, and the received emplacement data associated with the third emplacement sensor;

determine a second emplacement of the second virtual medical device with respect to the fourth coordinate system based at least in part on the received emplacement data associated with the second emplacement sensor, the predetermined offset, and the received emplacement data associated with the third emplacement sensor;

determine a second emplacement of the real-time medical imaging stream with respect to the fourth coordinate system based at least in part on the received emplacement data associated with the second emplacement sensor, the predetermined offset, and the received emplacement data associated with the third emplacement sensor;

cause a first opaque stereoscopic display of the head mounted display to display a first 3D rendered view of a virtual 3D scene including:
 a 3D rendering of the first virtual medical device based at least in part on the determined first emplacement of the first virtual medical device,
 a 3D rendering of the second virtual medical device based at least in part on the determined first emplacement of the second virtual medical device, and
 a 3D rendering of the real-time medical imaging stream based at least in part on the determined first emplacement of the real-time medical imaging stream; and cause a second opaque stereoscopic display of the head mounted display to display a second 3D rendered view of the virtual 3D scene including:
 a 3D rendering of the first virtual medical device based at least in part on the determined second emplacement of the first virtual medical device,
 a 3D rendering of the second virtual medical device based at least in part on the determined second emplacement of the second virtual medical device, and
 a 3D rendering of the real-time medical imaging stream based at least in part on the determined second emplacement of the real-time medical imaging stream, wherein the first 3D rendered view and the second 3D rendered view change in relation to a change in the emplacement data associated with the third emplacement sensor.

Clause 25. The guidance system of Clause 24, wherein the first emplacement sensor is associated with a first real medical device and the second emplacement sensor is associated with a second real medical device.

Clause 26. The guidance system of Clause 25, wherein the predetermined offset is configured to allow a wearer of the head mounted display to simultaneously view at least a portion of the first virtual medical device, and at least a portion of the real-time medical imaging stream on the first and second opaque stereoscopic displays, and at least a portion of a first medical device corresponding to the first virtual medical device and the second real medical device corresponding to the second virtual medical device at a location below the first and second opaque stereoscopic displays.

Clause 27. The guidance system of Clause 24, wherein the real-time medical imaging stream comprises at least one ultrasound image.

Clause 28. The guidance system of Clause 24, wherein the first opaque stereoscopic display is at least partially located within, and comprises only a subset of a field of view of a left eye of a wearer of the head mounted display, and wherein the second opaque stereoscopic display is at least partially located within, and comprises only a subset of, the field of view of a right eye of a wearer of the head mounted display.

Clause 29. A non-transitory computer-readable medium comprising computer executable instructions that when executed by one or more processors cause the one or more processors to:
 receive first emplacement data associated with a first emplacement sensor with respect to a first coordinate system;
 receive second emplacement data associated with a second emplacement sensor with respect to the first coordinate system;
 receive third emplacement data associated with a third emplacement sensor with respect to a second coordinate system, the third emplacement sensor associated with a user;
 determine an emplacement of a first virtual medical device with respect to a third coordinate system based at least in part on the first emplacement data, a offset, and the third emplacement data;
 determine an emplacement of a second virtual medical device with respect to the third coordinate system based at least in part on the second emplacement data, the offset, and the third emplacement data;
 receive a medical imaging stream associated with the second virtual medical device;
 determine an emplacement of the medical imaging stream with respect to the third coordinate system based at least in part on the second emplacement data, the offset, and the third emplacement data; and
 cause a display to display a 3D rendered view of a virtual 3D scene including:
  a 3D rendering of the first virtual medical device based at least in part on the determined emplacement of the first virtual medical device,
  a 3D rendering of the second virtual medical device based at least in part on the determined emplacement of the second virtual medical device, and
  a 3D rendering of the medical imaging stream based at least in part on the determined emplacement of the medical imaging stream,
 wherein the 3D rendered view changes in relation to a change in the third emplacement data.

Clause 30. The non-transitory computer-readable medium of Clause 29, wherein the first emplacement sensor is associated with a first real medical device and the second emplacement sensor is associated with a second real medical device.

Clause 31. The non-transitory computer-readable medium of Clause 30, wherein the offset is configured to allow a viewer of the display to simultaneously view at least a portion of the first virtual medical device and at least a portion of the medical imaging stream on the display, and at least a portion a medical device corresponding to the first virtual medical device above and/or below the display.

Clause 32. The non-transitory computer-readable medium of Clause 29, wherein the medical imaging stream comprises at least one ultrasound image.

Clause 33. A head mounted display, comprising:
 a frame configured to mount to a head of a user;
 a first opaque display coupled to the frame and located within a portion of a field of view of a left eye of the user when the frame is mounted to the head of the user, the first opaque display comprising only a subset of the field of view of the left eye of the user; and a second opaque display coupled to the frame and located within a field of view of a right eye of the user when the frame is mounted to the head of the user, the second opaque display comprising only a subset of the field of view of the right eye of the user, wherein the head mounted display is configured to enable the user to view an environment in the user's field of view not occupied by the first opaque display and the second opaque display.

Clause 34. The head mounted display of Clause 33, wherein the first opaque display is located within a central portion of the field of view of the left eye, and wherein the second opaque display is located within a central portion of the field of view of the right eye.

Clause 35. The head mounted display of Clause 33, wherein the first opaque display is configured to be movable within the field of view of the left eye, and wherein the second opaque display is configured to be movable within the field of view of the right eye.

Clause 36. The head mounted display of Clause 33, wherein the first opaque display occupies a portion of the field of view of the left eye of the user between 10 and 50 horizontal degrees and between 10 and 90 vertical degrees and the second opaque display occupies a portion of the field of view of the right eye of the user between 10 and 50 horizontal degrees and between 10 and 90 vertical degrees.

Clause 37. The head mounted display of Clause 33, wherein the head mounted display is configured to display on the first opaque display and the second opaque display a display object that is offset from a corresponding object in the environment.

Clause 38. The head mounted display of Clause 37, wherein the corresponding object is a medical device and the display object is a virtual medical device corresponding to the medical device.

Clause 39. A head mounted display, comprising:
a frame configured to mount to a head of a user; and
an opaque display adjustably coupled to the frame and located within a portion of a field of view of the user when the frame is mounted to the head of the user, the first opaque display comprising only a subset of the field of view of the user,
wherein the head mounted display is configured to enable the user to view an environment in the user's field of view not occupied by the opaque display.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, non-limiting examples: through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system 101. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, non-limiting examples: a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Virtualization technologies allow a single physical computing device to host one or more instances of a virtual machine, which virtual machine instance appears to a user as an independent computing device. With virtualization, the host computing device can create, maintain, delete, or otherwise manage virtual machines instances in a dynamic manner. In turn, users can request computing resources, including single computing devices or a configuration of networked computing devices, and be provided with virtual machine instances that provide the requested computing resources.

An instance of a virtual machine may be configured to provide specific functionality. For example, a virtual machine instance may be associated with different combinations of software applications and operating systems or operating system configurations to enable a virtual machine to provide different desired functionalities, or to provide similar functionalities more efficiently.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention may be recited as a means-plus-function claim under 35 U.S.C sec. 112(f) (AIA), other aspects may likewise be embodied as a means-plus-function claim, or in other forms, such as being embodied in a computer-readable medium. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application, in either this application or in a continuing application.

Disjunctive language such as the phrase "at least one of X, Y, or Z," unless specifically stated otherwise, is otherwise understood with the context as used in general to present that an item, term, etc., may be either X, Y, or Z, or any combination thereof (non-limiting examples: X, Y, and/or Z). Thus, such disjunctive language is not generally intended to, and should not, imply that certain embodiments require at least one of X, at least one of Y, or at least one of Z to each be present.

Unless otherwise explicitly stated, articles such a "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The previous description of the disclosed implementations is provided to enable a person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments

The invention claimed is:

1. A guidance system, comprising one or more processors, the guidance system configured to:
    determine an emplacement of a first medical display object with respect to a first coordinate system based at least in part on a first offset, an emplacement of a first emplacement sensor with respect to a second coordinate system, and an emplacement of a second emplacement sensor with respect to a third coordinate system;
    determine an emplacement of a second medical display object with respect to the first coordinate system based at least in part on a second offset and an emplacement of the second emplacement sensor with respect to the third coordinate system; and
    cause a display to display:
        a rendering of at least a portion of the first medical display object based at least in part on the emplacement of the first medical display object, wherein the rendering of the at least a portion of the first medical display object varies in response to a change in at least one of the emplacement of the first emplacement sensor with respect to the second coordinate system or the emplacement of the second emplacement sensor with respect to the third coordinate system; and
        a rendering of at least a portion of the second medical display object based at least in part on the emplacement of the second medical display object, wherein the rendering of the at least a portion of the second medical display object varies responsive to the change in the emplacement of the second emplacement sensor with respect to the third coordinate system.

2. The guidance system of claim 1, wherein the first medical display object comprises at least one of a medical device, a virtual medical device, or a medical image.

3. The guidance system of claim 1, wherein the first emplacement sensor is associated with a medical device, and wherein the second emplacement sensor is associated with a head mounted display.

4. The guidance system of claim 1, wherein each of the first coordinate system, the second coordinate system, and the third coordinate system is a different coordinate system.

5. The guidance system of claim 1, wherein the second medical display object comprises at least one of a medical device, a virtual medical device, or a medical image.

6. The guidance system of claim 1, wherein the first emplacement sensor is associated with a first medical device and wherein the second emplacement sensor is associated with a head mounted display.

7. The guidance system of claim 1, wherein a viewer of the display can simultaneously view the rendering of the at least a portion of the medical display object and at least a portion of the medical display object above and/or below the display.

8. A method of presenting virtual content to a user, the method comprising:
    determining an emplacement of a first medical display object with respect to a first coordinate system based at least in part on a first offset and first emplacement data, wherein the first emplacement data corresponds to an emplacement of a first emplacement sensor with respect to a second coordinate system;
    determining an emplacement of a second medical display object with respect to the first coordinate system based at least in part on a second offset and second emplacement data, wherein the second emplacement data corresponds to an emplacement of a second emplacement sensor with respect to a third coordinate system; and
    causing a display to display a 3D rendering based at least in part on the emplacement of the first medical display object and the second medical display object, wherein the 3D rendering comprises at least a portion of the first medical display object and at least a portion of the second medical display object, wherein the 3D rendering changes in response to a change in the emplacement of the first emplacement sensor with respect to the first coordinate system, wherein the 3D rendering changes in response to a change in the emplacement of the second emplacement sensor with respect to the third coordinate system.

9. The method of claim 8, wherein at least one of the first medical display object or the second medical display object comprises at least one of a medical device, a virtual medical device, or a medical image.

10. The method of claim 8, wherein the first emplacement sensor is associated with a medical device, and wherein the second emplacement sensor is associated with a head mounted display.

11. The method of claim 8, wherein each of the first coordinate system, the second coordinate system, and the third coordinate system is a different coordinate system.

12. The method of claim 8, wherein said determining the emplacement of the first medical display object is further based at least in part on an emplacement of the second emplacement sensor with respect to the third coordinate system.

13. The method of claim 8, wherein the second medical display object comprises an ultrasound image.

14. The method of claim 8, wherein a viewer of the display can simultaneously view the 3D rendering and at least a portion of the medical display object above and/or below the display.

15. Non-transitory computer-readable media storing computer executable instructions that when executed by one or more processors cause the one or more processors to:
    determine an emplacement of a first medical display object with respect to a first coordinate system based at least in part on a first offset and first emplacement data, wherein the first emplacement data corresponds to an emplacement of a first emplacement sensor with respect to a second coordinate system;
    determine an emplacement of a second medical display object with respect to the first coordinate system based at least in part on a second offset and second emplacement data, wherein the second emplacement data corresponds to an emplacement of a second emplacement sensor with respect to a third coordinate system; and
    cause a display to display a 3D rendering based at least in part on the emplacement of the first medical display object and the second medical display object, wherein the 3D rendering comprises at least a portion of the first medical display object and at least a portion of the second medical display object, wherein the 3D rendering changes in response to a change in the emplacement of the first emplacement sensor with respect to the first coordinate system, wherein the 3D rendering changes in response to a change in the emplacement of the second emplacement sensor with respect to the third coordinate system.

16. The non-transitory computer-readable media of claim 15, wherein at least one of the first medical display object or the second medical display object comprises at least one of a medical device, a virtual medical device, or a medical image.

17. The non-transitory computer-readable media of claim 15, wherein the first emplacement sensor is associated with a medical device, and wherein the second emplacement sensor is associated with a head mounted display.

18. The non-transitory computer-readable media of claim 15, wherein each of the first coordinate system, the second coordinate system, and the third coordinate system is a different coordinate system.

19. The non-transitory computer-readable media of claim 15, to determine the emplacement of the first medical display object, the one or more processors are configured to determine the emplacement of the first medical display object based at least in part on an emplacement of the second emplacement sensor with respect to the third coordinate system.

20. The non-transitory computer-readable media of claim 15, wherein the second medical display object comprises an ultrasound image.

* * * * *